United States Patent [19]

Kump et al.

[11] Patent Number: 5,003,070
[45] Date of Patent: Mar. 26, 1991

[54] SUBSTITUTED AZACYCLOHEXYL DERIVATIVES OF RIFAMYCINS

[75] Inventors: Wilhelm Kump, Biel-Benken, Switzerland; Jen Chen, Middlesex, N.J.

[73] Assignee: Ciba-Geigy Corporation, Ardsley, N.Y.

[21] Appl. No.: 343,980

[22] Filed: Apr. 26, 1989

[30] Foreign Application Priority Data

Jun. 30, 1988 [CH] Switzerland .................. 2500/88
Mar. 2, 1989 [CH] Switzerland .................... 776/89

[51] Int. Cl.⁵ ............... A61K 31/495; A61K 31/445; C07D 498/18
[52] U.S. Cl. .................... 544/368; 514/824; 544/360; 544/364; 546/198
[58] Field of Search ............ 546/198; 514/321, 824, 514/254; 544/368, 360, 364

[56] References Cited

U.S. PATENT DOCUMENTS

| | | | |
|---|---|---|---|
| 4,005,077 | 1/1977 | Bickel et al. | 514/924 |
| 4,327,096 | 4/1982 | Marsili et al. | 514/924 |
| 4,353,826 | 10/1982 | Bickel et al. | 514/924 |

OTHER PUBLICATIONS

Abstract of WO-A-8,702,361.
Chemical Pharmaceutical Bulletin, vol. 33, No. 5, pp. 2133–2136 (1965).
Abstract of EPA 314,624.

*Primary Examiner*—Cecilia Shen
*Attorney, Agent, or Firm*—JoAnn Villamizar

[57] ABSTRACT

The invention relates to novel substituted azacyclohexyl derivatives of formula

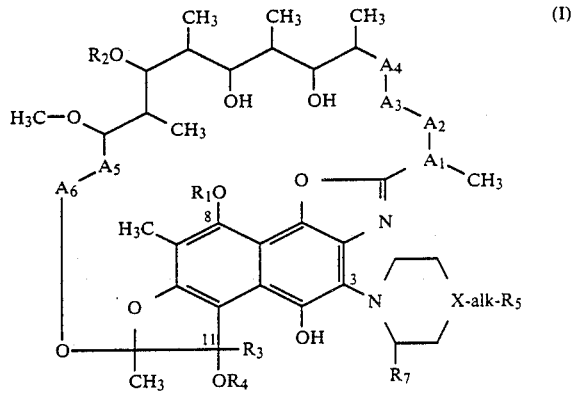

and salts of thereof in which the structural elements $-A_1-A_2-$, $-A_3-A_4-$ and $-A_5-A_6-$ are each ethylene or vinylene or the elements $-A_1-A_2-$ and $-A_3-A_4-$ are each ethylene and $-A_5-A_6-$ is vinylene, X is $>CR_6-$ or $>N-$ and $R_6$ is alkyl or hydrogen, alk is an aliphatic hydrocarbon radical or a bond, $R_1$ is hydrogen or acyl, $R_2$ is hydrogen or acetyl, $R_3$ and $R_4$ together are a bond or each is hydrogen, $R_5$ is hydrogen, a cycloaliphatic hydrocarbon radical, aryl or heteroaryl and $R_7$ is hydrogen or alkyl, with the proviso that when $-A_1-A_2-$, $-A_3-A_4-$ and $-A_5-A_6-$ are each vinylene, X is $>N-$, $R_1$ is hydrogen or trialkylacetyl, $R_2$ is hydrogen or acetyl, $R_3$ and $R_4$ together are a bond and alk is methylene, $R_5$ is other than 2,6-dimethyl-4-alkylphenyl, which can be used as active ingredients in medicaments, to their preparation and use and to pharmaceutical preparations.

44 Claims, No Drawings

SUBSTITUTED AZACYCLOHEXYL DERIVATIVES OF RIFAMYCINS

The present invention relates to novel substituted azacyclohexyl derivatives of rifamycins of formula

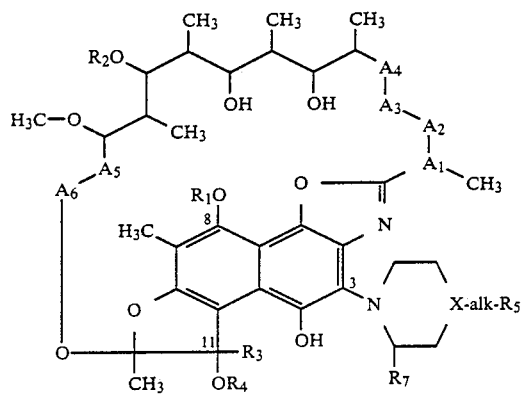

and salts thereof in which the structural elements $—A_1-A_2—$, $—A_3-A_4—$ and $—A_5-A_6—$ are each ethylene or vinylene or the elements $—A_1-A_2—$ and $—A_3-A_4—$ are each ethylene and $—A_5-A_6—$ is vinylene, X is $>CR_6—$ or $>N—$ and $R_6$ is alkyl or hydrogen, alk is an aliphatic hydrocarbon radical or a bond, $R_1$ is hydrogen or acyl, $R_2$ is hydrogen or acetyl, $R_3$ and $R_4$ together are a bond or each is hydrogen, $R_5$ is hydrogen, a cycloaliphatic hydrocarbon radical, aryl or heteroaryl and $R_7$ is hydrogen or alkyl, with the proviso that when $—A_1-A_2—$, $—A_3-A_4—$ and $—A_5-A_6—$ are each vinylene, X is $>N—$, $R_1$ is hydrogen or trialkylacetyl, $R_2$ is hydrogen or acetyl, $R_3$ and $R_4$ together are a bond and alk is methylene, $R_5$ is other than 2,6-dimethyl-4-alkylphenyl, to their preparation and use and to pharmaceutical preparations and the manufacture thereof.

The basic numbering of the ring system corresponds to that used, for example, in U.S. Pat. No. 4,005,077. The compounds of formula I contain a number of chirality centres, and accordingly the present invention also includes the corresponding optical isomers, for example diastereoisomers.

The compounds of formula I may be in the form of salts, especially pharmaceutically acceptable salts. As the compounds of this invention contain at least one basic centre they are able to form acid addition salts. Such salts are formed, for example, with inorganic acids, such as mineral acids, for example sulfuric acid, a phosphoric or hydrohalic acid, or with organic carboxylic acids, such as $C_1$–$C_4$alkanecarboxylic acids that are unsubstituted or substituted, for example, by halogen, for example acetic acid; or such as unsaturated or saturated dicarboxylic acids, for example oxalic, malonic, succinic, maleic, fumaric, phthalic or terephthalic acid; hydroxycarboxylic acids, for example ascorbic acid, glycolic acid, lactic acid, malic acid, tartaric acid or citric acid; amino acids, for example aspartic acid or glutamic acid; or aromatic carboxylic acids, for example benzoic acid; or with organic sulfonic acids, such as unsubstituted or, for example, halo-substituted, $C_1$–$C_4$alkane- or aryl-sulfonic acids, for example methanesulfonic acid, bromobenzenesulfonic acid or toluenesulfonic acid. Corresponding acid addition salts can also be formed with a basic centre that may be present in addition (for example $X = >N—$). Further, the compounds of the invention containing an acid phenolic hydroxy group can form salts with bases, for example alkali metal salts, such as sodium or potassium salts. In addition, corresponding internal salts can be formed. Salts that are unsuitable for pharmaceutical purposes are also included, since these salts can be used, for example, for the isolation and purification of compounds of the invention or the pharmaceutically acceptable salts thereof. An aliphatic hydrocarbon radical is especially alkylene, alkenylene or alkynylene, the multiple bonds preferably being located in a position higher than the α-position to the piperazine nitrogen atom ($X = >N—$) in unsaturated radicals.

Acyl is derived, for example, from an organic carboxylic acid or from a substituted carbonic acid. Such radicals are, for example, unsubstituted or, for example, halo- or aryl-substituted ($C_1$–$C_7$-)alkanoyl, or unsubstituted or, for example, halo-, ($C_1$–$C_7$-)alkyl-, ($C_1$–$C_7$-)alkoxy-, hydroxy-, ($C_2$–$C_8$-)alkanoyloxy-, trifluoromethyl- and/or nitrosubstituted carbocyclic aroyl, such as benzoyl or naphthoyl, or heterocyclic aroyl, such as monocyclic, 5- or 6-membered monothia-, monooxa-, or monoaza-aroyl, for example (2-)thenoyl, (3-)furoyl, nicotinoyl or isonicotinoyl. A suitable acyl radical derived from a substituted acid is, for example, ($C_1$–$C_7$-)alkoxycarbonyl, or aminocarbonyl that is unsubstituted or mono- or di-substituted, for example, by ($C_1$–$C_7$-)alkyl.

A cycloaliphatic hydrocarbon radical is especially cycloalkyl, cycloalkenyl or cycloalkynyl, it being possible for such radicals to contain, in addition, one or more, such as 2 or 3, alkyl groups, especially lower alkyl.

Aryl is derived, for example, from a mono- or polycyclic, C-ring system that contains at least one aromatic ring, such as phenyl, biphenylyl, such as 2-, 3-or, especially, 4-biphenylyl, or naphthyl, such as 1- or 2- naphthyl, and is unsubstituted or mono- or polysubstituted, for example di- or tri-substituted, for example by halogen, ($C_1$–$C_7$-)alkyl, ($C_1$–$C_7$-)alkoxy, hydroxy, ($C_2$–$C_8$-)alkanoyloxy, trifluoromethyl and/or nitro.

Heteroaryl is especially monocyclic 5- or 6-membered monoaza- monooxa- or monothia-aryl, such as pyrrolyl, N-alkylpyrrolyl, pyridyl, N-oxido-pyridyl, furyl or thienyl and is unsubstituted or mono- or polysubstituted, such as di- or tri-substituted, for example as indicated for aryl.

The general definitions used hereinbefore and hereinafter have, unless defined otherwise, especially the following meanings:

Alkyl is especially $C_1$–$C_7$alkyl and is, for example, methyl, ethyl, propyl, isopropyl, n-butyl, isobutyl, sec.-butyl or tert.-butyl and also includes corresponding pentyl, hexyl and heptyl radicals. $C_1$–$C_4$alkyl is preferred.

Alkylene is, for example, $C_1$–$C_{12}$alkylene, especially $C_1$–$C_7$alkylene, and is straight-chain or branched and is, for example, methylene, ethylene, propylene or butylene as well as 1,2-propylene, 2-methyl-1,3-propylene or 2,2-dimethyl,3-propylene. $C_1$–$C_4$alkylene, especially methylene, is preferred.

Alkenylene is especially $C_3$–$C_7$alkenylene, is straight chain or branched and is, for example 1,3-prop-2-enylene, 1,4-but-2- or 1,4-but-3-enylene, 1,3-but-2-enylene, 2,4-but-3-enylene, 1,5-pent-2-, 3- or -4-enylene, and also corresponding hexenylene and heptenylene radicals. $C_3-C_5$alkenylene is preferred.

Alkynylene is especially $C_3-C_7$is straight-chain or branched and is, for example 1,3-prop-2-ynylene, 1,4-but-2- or 1,4-but-3-ynylene, 1,5-pent-2-, -3- or -5-ynylene, and also corresponding hexynylene and heptynylene radicals. $C_3-C_5$alkynylene is preferred.

Halogen is especially halogen having an atomic number of up to and including 35, such as fluorine, chlorine or bromine, and also iodine.

Cycloalkyl is especially $C_3-C_7$cycloalkyl, for example cyclopropyl, cyclobutyl, cyclopentyl, cyclohexyl or cycloheptyl. Cyclopentyl and cyclohexyl are preferred.

Cycloalkenyl is especially $C_3-C_7$cycloalkenyl and contains especially one, or also (from $C_4$) two double bonds, for example cycloprop-2-en-1-yl, cyclobut-2-en-1-yl, cyclobut1,3-dien-1-yl, cyclopent-2-en-1-yl, -3-en-1-yl, -2,4-dien1-yl, cyclohex-2-en-1-yl, -3-en-1-yl or -2,4-dien-1-yl, -1,3-dien-1-yl or -2,5-dien-1-yl, or also a corresponding cycloheptenyl radical.

Cycloalkynyl is especially $C_3-C_7$cycloalkynyl and contains especially a triple bond, and is, for example, cyclopent-2-yn-1-yl, cyclobut-2-yn-1-yl, cyclopent-2-yn-1-yl or -3-yn1-yl, cyclohex-2-yn-1-yl or -3-yn-1-yl, or a corresponding heptynyl radical.

Alkanoyl is especially $C_2-C_8$alkanoyl and is, for example, acetyl, propionyl, butyryl, isobutyryl or pivaloyl. Branched $C_3-C_6$alkanoyl, especially pivaloyl, is preferred.

Alkoxy is especially $C_1-C_7$alkoxy and is, for example methoxy, ethoxy, propoxy, isopropoxy, n-butoxy, isobutoxy or tert.-butoxy. $C_1-C_4$alkoxy is preferred.

In alkanoyloxy, alkanoyl has the meanings given hereinbefore.

In alkoxycarbonyl alkoxy has the meanings given hereinbefore.

Pyrrolyl is, for example, 1-, 2- or 3-pyrrolyl, pyridyl is, for example, 2-, 3- or 4-pyridyl, 1-oxido-pyridyl is, for example, 1-oxido-2-, -3- or -4-pyridyl, furyl is, for example, 2- or 3-furyl and thienyl is, for example 2- or 3-thienyl.

Derivatives that are derived, for example, from rifamycin SV, are known to have pronounced antibiotic properties and can be used, for example, for the treatment of tuberculosis. It has now been found that the compounds of formula I and the pharmaceutically acceptable salts thereof do not exhibit any corresponding antibiotic activity in the conventional pharmacological test models for assessment.

Surprisingly, however, they do have a significant lipid-lowering activity, which can be demonstrated in animal tests, preferably carried out on mammals, for example rats. Thus, the lowering of very low density, low density and high density lipoproteins (VLDL, LDL and HDL) in serum can be demonstrated in two test procedures, in male rats with genetic hypercholesterolaemia (procedure A) and in normolipaemic rats of both sexes (procedure B).

Albino rats having a body weight of 180–240 g and with free access to standard rat feed and drinking water are used. For procedure A, the rats are Sprague Dawley progeny of the Tif:RAI strain and, for procedure B, are animals of the IVa-WI Wistar strain. The test compound is administered orally to groups of 8 to 10 rats, daily for 5 consecutive days, in a polyethylene glycol solution (average molecular weight: 400). Two hours after the final administration the animals, anaesthetised with ether, are sacrificed by being bled from the throat. For a period of 16 hours before being sacrificed the animals receive no more food. To the combined serum of 2 to 3 rats there are added a 0.05% aqueous solution of ethylenediaminetetraacetic acid and a 0.01% aqueous solution of thiomersal. Using an ultra-centrifuge, the serum lipoproteins are separated by centrifuging for 24 hours at 78,000 g, 78,000 g or 109,000 g in salt solutions with densities of 1.006 and 1.040, respectively, and are analysed enzymatically for their content of cholesterol and triglycerides using test systems supplied, for example, by Sigma Chemical Co. (St. Louis, Mo. U.S.A.).

The test for antibiotic activity is carried out, for example, on the one hand in vitro by determining the mean effective concentration $EC_{50}$ for the inhibition of the RNA polymerase of *Escherichia coli*, as well as the minimum inhibitory concentration MIC in the conventional plate test, and, on the other hand, in vivo by determining the $ED_{50}$ (effective dose that is life-preserving for 50% of the test animals) in infected mice and rats. The microorganisms used for this purpose are especially *Mycobacterium tuberculosis* TB $H_{37}Rv$ and *Staphylococcus aureus*. When using compounds having a lipid-lowering indication, an antibiotic activity is considered a disadvantage, as it can lead to the formation of strains of microorganisms that are resistant to antibiotics, especially in the case of longterm administration.

In the above-described test methods, the compounds of the invention, when administered repeatedly in the dosage range of from about 0.1 to about 50 mg/kg per day, exhibit a significant hypolipidaemic activity; on the other hand, they are free from any noticeable antibiotic activity in the above-mentioned tests.

Thus, for example, it can be shown that, depending on the test procedure, the minimum effective dose of the compounds of the invention when administered in a single dose is from about 0.1 to about 10 mg/kg, and that a 50–70% lowering of the LDL fraction can be achieved by repeated administration of 30 mg/kg daily. The compounds in this case have virtually no antibiotic activity; an $EC_{50}$ for the inhibition of RNA polymerase is still not attained with 100 μg/ml, and the MIC for various pathogenic strains of Staphylococcus aureus is higher than 130 μg/ml. Such values are about 1000 times higher than concentrations normally required for a corresponding effect. Even under in vivo conditions using mice infected with Staphylococcus aureus, the compound exhibits no antibiotic activity when administered in a single dose of 200 mg/kg.

Especially on account of their LDL-lowering activity, the compounds of this invention can be used, for example, as hypolipidaemic agents for the treatment of hyperlipidaemiae, mainly of types IIa and IIb, and arteriosclerosis, for example when hyperlipoproteinaemia is a risk factor.

Accordingly, the compounds of formula I and the pharmaceutically acceptable salts thereof can be used, for example, as pharmaceutical agents, for example as hypolipidaemic agents for the treatment of hyperlipidaemiae, mainly of types IIa and IIb, and of arteriosclerosis when hyperlipoproteinaemia is a risk factor. The invention further relates to the use of the compounds of the invention for the preparation of medicaments, especially hypolipidaemic agents and antiarteriosclerosis agents, and for therapeutic and prophylactic treatment. The commercial manufacture of the active substances also falls within the scope of this invention.

The invention relates especially to compounds of formula I and salts thereof in which $-A_1-A_2-$, —$A_3$–$A_4$—, —$A_5$–$A_6$—, $R_2$, $R_3$ and $R_4$ have the meanings given, X is >CH— or >N—, alk is alkylene, $R_1$ is hydrogen or acyl, $R_5$ is hydrogen, cycloalkyl or aryl, and $R_7$ is hydrogen. The invention relates especially to compounds of formula I salts thereof in which —$A_1$–$A_2$—, —$A_3$–$A_4$—, —$A_5$–$A_6$—, $R_2$, $R_3$ and $R_4$ have the meanings given, X is >C($R_6$) or >N— and $R_6$ is hydrogen or alkyl, alk is alkylene, alkenylene or alkynylene, the multiple bond being located in a position higher than the α-position to the piperazine nitrogen (X==>N—), $R_1$ is unsubstituted or halo- or phenyl-substituted alkanoyl, benzoyl, naphthoyl or monocyclic 5- or 6-membered monoaza-, monooxa- or monothia-aroyl, alkoxycarbonyl, or aminocarbonyl that is unsubstituted or mono- or di-substituted by alkyl, $R_5$ is hydrogen, cycloalkyl, cycloalkenyl, cycloalkynyl, phenyl, biphenylyl, naphthyl, monocyclic 5- or 6-membered monoaza-, monooxa- or monothiaaryl and $R_7$ is hydrogen or alkyl, each of the aromatic radicals, independently of the others, being unsubstituted or mono- or poly-substituted by halogen, alkyl, alkoxy, hydroxy, alkanoyloxy, trifluoromethyl and/or nitro.

The invention relates especially to compounds of formula I and salts thereof in which —$A_1$–$A_2$—, —$A_3$–$A_4$—, —$A_5$–$A_6$—, $R_2$, $R_3$ and $R_4$ have the meanings given, X is >C($R_6$) or >N— and $R_6$ is hydrogen or $C_1$–$C_7$alkyl, alk is $C_1$–$C_{12}$alkylene, $C_3$–$C_7$alkenylene or $C_3$–$C_7$alkynylene, the multiple bond being located in a position higher than the α-position to the piperazine nitrogen atom, $R_1$ is unsubstituted or halo- or phenyl-substituted $C_2$–$C_8$alkanoyl, benzoyl, naphthoyl or monocyclic 5- or 6-membered monoaza-, monooxa- or monothiaaroyl, $C_1$–$C_7$alkoxycarbonyl, or aminocarbonyl that is unsubstituted or mono- or di-substituted by $C_1$–$C_7$alkyl, $R_5$ is hydrogen, $C_3$–$C_7$cycloalkyl, $C_3$–$C_7$-cycloalkenyl, $C_3$–$C_7$-cycloalkynyl, phenyl, biphenylyl, naphthyl, pyrrolyl, N-$C_1$–$C_7$alkylpyrrolyl, pyridyl, 1-oxidopyridyl, furyl or thienyl, and $R_7$ is hydrogen or $C_1$–$C_7$alkyl, each of the aromatic radicals, independently of the others, being unsubstituted or mono- or poly-substituted by halogen, $C_1$–$C_7$alkyl, $C_1$–$C_7$alkoxy, hydroxy, $C_2$–$C_8$alkanoyloxy, trifluoromethyl and/or nitro. The invention relates especially to compounds of formula I and salts thereof in which —$A_1$–$A_2$—, —$A_3$–$A_4$—, —$A_5$–$A_6$—, $R_2$, $R_3$ and $R_4$ have the meanings given, X is >CH— or >N—, alk is $C_1$–$C_7$alkylene, $R_1$ is $C_2$–$C_8$alkanoyl that is unsubstituted or substituted by halogen or by phenyl which may contain halogen, $C_1$–$C_7$alkyl, $C_1$–$C_7$alkoxy, hydroxy, $C_2$–$C_8$alkanoyloxy, trifluoromethyl and/or nitro, unsubstituted or halo-, $C_1$–$C_7$alkyl-, $C_1$–$C_7$alkoxy-, hydroxy-, $C_2$–$C_8$alkanoyloxy, trifluoromethyl- and/or nitro-substituted benzoyl, naphthoyl or monocyclic 5- or 6-membered monoazao-, monooxa- or monothia-aroyl, $C_1$–$C_7$alkoxycarbonyl, or aminocarbonyl that is unsubstituted or mono- or di-substituted by $C_1$–$C_7$alkyl, $R_5$ is hydrogen, $C_3$–$C_7$cycloalkyl, or phenyl, biphenylyl or naphthyl each of which is unsubstituted or mono- or polysubstituted by halogen, $C_1$–$C_7$alkyl, $C_1$–$C_7$alkoxy, hydroxy, $C_2$–$C_8$alkanoyloxy, trifluoromethyl and/or by nitro, and $R_7$ is hydrogen.

The invention relates especially to compounds of formula I and salts thereof in which —$A_1$–$A_2$—, —$A_3$–$A_4$—, —$A_5$–$A_6$—, $R_2$, $R_3$ and $R_4$ have the meanings given, X is >C($R_6$) or >N— and $R_6$ is hydrogen or $C_1$–$C_7$alkyl, alk is $C_1$–$C_{12}$alkylene, such as $C_1$–$C_7$alkylene, $C_3$–$C_7$alkenylene or $C_3$–$C_7$alkynylene, the multiple bond being located in a position higher than the α-position to the piperazine nitrogen atom, $R_1$ is hydrogen or $C_3$–$C_6$alkanoyl, $R_5$ is hydrogen, $C_3$–$C_7$cycloalkyl, $C_3$–$C_7$cycloalkenyl, or phenyl, biphenylyl, naphthyl, thienyl, furyl or pyridyl each of which is unsubstituted or substituted by halogen, $C_1$–$C_7$alkyl, $C_1$–$C_7$alkoxy and/or by trifluoromethyl, and $R_7$ is hydrogen or $C_1$–$C_7$alkyl.

The invention relates especially to compounds of formula I and salts thereof in which —$A_1$–$A_2$—, —$A_3$–$A_4$—, —$A_5$–$A_6$—, $R_3$ and $R_4$ have the meanings given, X is >CH— or >N—, $R_1$ is $C_3$–$C_6$alkanoyl, especially pivaloyl, $R_2$ is acetyl, on the one hand alk is $C_3$–$C_7$alkylene, such as 2-methyl-1,3-propylene, and $R_5$ is hydrogen, or on the other hand alk is $C_1$–$C_4$alkylene, especially methylene, and $R_5$ is $C_3$–$C_6$cycloalkyl, such as cyclohexyl, $C_3$–$C_6$cycloalkenyl, such as cyclohex-3-en-1-yl, unsubstituted or $C_1$–$C_4$alkyl-substituted, especially methyl-substituted, phenyl, such as 2,5-dimethyl- or 2,4,6-trimethylphenyl, biphenylyl, such as 4-biphenylyl, naphthyl, such as 2-naphthyl, or thienyl, such as 2-thienyl, and $R_7$ is hydrogen or $C_1$–$C_4$alkyl, such as methyl.

The invention relates especially to compounds of formula I and salts thereof in which —$A_1$–$A_2$—, —$A_3$–$A_4$—, —$A_5$–$A_6$—, $R_3$ and $R_4$ have the meanings given, $R_1$ is hydrogen or $C_2$–$C_8$alkanoyl, especially branched $C_3$–$C_6$alkanoyl, $R_2$ is acetyl, X is >N—, alk is $C_1$–$C_7$alkylene, especially $C_1$–$C_4$alkylene, $R_5$ is hydrogen, $C_3$–$C_7$cycloalkyl, or phenyl, biphenylyl or naphthyl each of which is unsubstituted or mono- or poly-substituted by $C_1$–$C_4$alkyl or halogen, and $R_7$ is hydrogen.

The invention relates especially to compounds of formula I and salts thereof in which the structural elements —$A_1$–$A_2$—, —$A_3$–$A_4$— and —$A_5$–$A_6$—have the meanings given, $R_1$ is branched $C_3$–$C_6$alkanoyl, such as pivaloyl, $R_2$ is acetyl, $R_3$ and $R_4$ have the meanings given, X is >N—, alk is $C_1$–$C_4$alkylene, such as methylene, $R_5$ is $C_3$–$C_7$cycloalkyl, such as cyclohexyl, $C_3$–$C_7$-cycloalkenyl, such as cyclohex-3-en-1-yl, or phenyl mono- or poly-substituted, such as di- or trisubstituted, by $C_1$–$C_4$alkyl, such as methyl, such as 2-methylphenyl, 2,3-, 2,5- or 2,6-dimethylphenyl or 2,4,6-trimethylphenyl, and $R_7$ is on the one hand hydrogen, or on the other hand $C_1$–$C_4$alkyl, such as methyl.

The invention relates especially to compounds of formula I and salts thereof in which the structural elements —$A_1$–$A_2$—, —$A_3$–$A_4$— and —$A_5$–$A_6$— and the variables $R_3$ and $R_4$ have the meanings given, alk is $C_1$–$C_4$alkylene, such as methylene, 2,3-propylene or 2-methyl-1,3-propylene, $R_1$ is hydrogen or branched $C_3$–$C_6$alkanoyl, such as pivaloyl, $R_2$ is acetyl, X is >N—, $R_5$ is hydrogen, $C_3$–$C_6$cycloalkyl, such as cyclois hexyl, phenyl or 2,4,6-tri-$C_1$–$C_4$alkylphenyl, such as 2,4,6-trimethylphenyl, and $R_7$ is hydrogen.

The invention relates especially to compounds of formula I and salts thereof in which the structural elements —$A_1$–$A_2$—, —$A_3$–$A_4$— and —$A_5$–$A_6$—have the meanings given, X is >N—, $R_2$ is hydrogen or acetyl, $R_3$ and $R_4$ together are a bond, and on the one hand alk is $C_1$–$C_4$alkylene, especially 2-methyl1,3-propylene and $R_5$ is hydrogen, or on the other hand alk is methylene and $R_5$ is 2,4,6-tri-$C_1$–$C_4$alkylphenyl, especially 2,4,6-trimethylphenyl, and $R_7$ is in each case hydrogen.

The invention relates especially to compounds of formula I and salts thereof in which the structural elements —$A_1$–$A_2$—, —$A_3$–$A_4$— and —$A_5$–$A_6$—have the meanings given, X is >N—, $R_2$ is acetyl, $R_3$ and $R_4$ together are a bond or each is hydrogen, and on the one hand alk is $C_1-C_4$alkylene, especially 2-methyl-1,3-propylene, and $R_5$ is hydrogen, or on the other hand alk is methylene and $R_5$ is 2,4,6-tri$C_1-C_4$alkylphenyl, especially 2,4,6-trimethylphenyl, and $R_7$ is in each case $C_1-C_4$alkyl, such as methyl.

The invention relates especially to compounds of formula I and salts thereof in which the structural elements $-A_1-A_2-$, $-A_3-A_4-$ and $-A_5-A_6-$ are each vinylene, or the elements $-A_1-A_2-A_3-A_4-$ are buta-1,3-dien-1,4-diyl and $-A_5-A_6-$ is ethylene, X is $>N-$, alk is $C_1-C_4$alkylene, especially methylene or 2,3-propylene, $R_1$ is branched $C_3-C_6$alkanoyl, especially pivaloyl, $R_2$ is acetyl, $R_3$ and $R_4$ together are a bond and $R_5$ is hydrogen, or also cyclohexyl or phenyl, and $R_7$ is hydrogen.

The invention relates especially to compounds of formula I and salts thereof in which the structural elements $-A_1-A_2-$, $-A_3-A_4-$ and $-A_5-A_6-$ are each vinylene, or the elements $-A_1-A_2-A_3-A_4-$ are buta-1,3-dien-1,4-diyl and $-A_5-A_6-$ is ethylene, X is $>N-$, $R_1$ is hydrogen or branched $C_3-C_6$alkanoyl, especially pivaloyl, $R_2$ is acetyl, $R_3$ and $R_4$ together are a bond, alk is $C_1-C_4$alkylene, especially 2-methyl-1,3-propyl, and $R_5$ is hydrogen, or alk is $C_1-C_4$-alkylene, especially methylene and $R_5$ is 2,4,6-tri$C_1-C_4$alkylphenyl, especially 2,4,6-trimethylphenyl, and $R_7$ is hydrogen.

The invention relates especially to compounds of formula I and salts thereof in which X is $>N-$, $-A_1-A_2-$ and $-A_3-A_4-$ are each ethylene and $-A_5-A_6-$ is vinylene or ethylene, $R_1$ is branched $C_3-C_6$alkanoyl, especially pivaloyl, $R_2$ is acetyl, $R_3$ and $R_4$ together are a bond or each is hydrogen, on the one hand alk is $C_1-C_4$alkylene, especially methylene, and $R_5$ is 2,4,6-trimethylphenyl, or on the other hand alk is $C_1-C_4$alkylene, especially 2-methyl-1,3-propylene, and $R_5$ is hydrogen, and $R_7$ is hydrogen.

The invention relates especially to compounds of formula I and salts thereof in which $-A_1-A_2-$, $-A_3-A_4-$ and $-A_5-A_6-$ are each ethylene, X is $>N-$, $R_1$ is pivaloyl, $R_2$ is acetyl, $R_3$ and $R_4$ together are a bond or each is hydrogen, alk-$R_5$ is 2,4,6-trimethylbenzyl, and $R_7$ is hydrogen.

The conditions of exclusion mentioned at the beginning apply also to the above-defined compounds of formula I and salts thereof.

The invention relates especially to the novel compounds mentioned in the Examples and to the preparation thereof. The invention further relates to processes for the preparation of the compounds of the invention. The preparation of compounds of formula I and salts thereof is carried out in a manner known per se and comprises, for example, (a) for the preparation of compounds of formula I and salts thereof in which X represents $>N-$, reacting a compound of formula

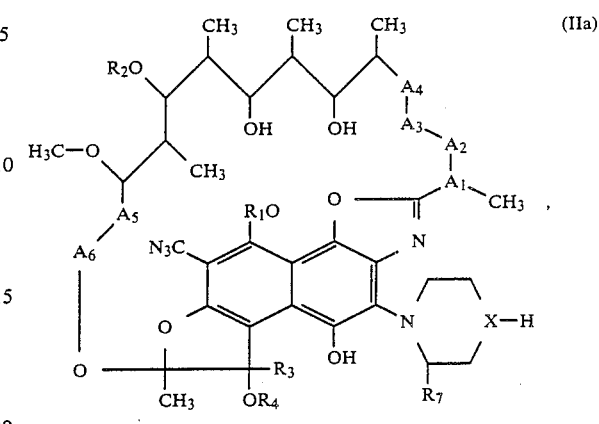

or a salt thereof in which X is $>N-$, with a compound of formula $$Z-alk-R_5 \qquad (IIb)$$

in which Z is reactive esterified hydroxy or (b) for the preparation of compounds of formula I and salts thereof in which $R_2$ is acetyl and $R_3$ and $R_4$ together are a bond, cyclising a compound of formula

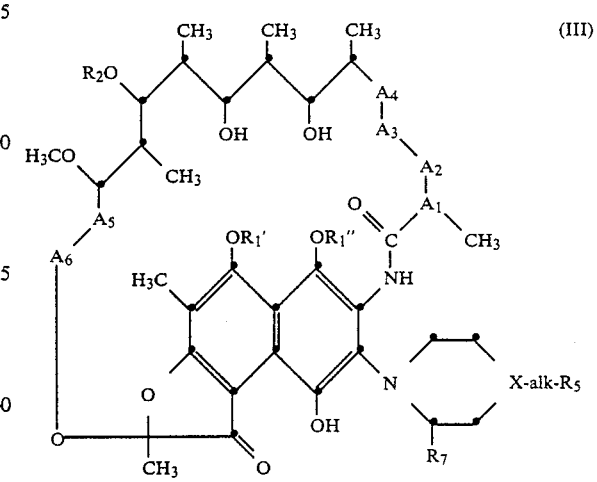

in which $R_1'$ is acyl and $R''_1$ is hydrogen or acyl, or (c) cyclising a compound of formula

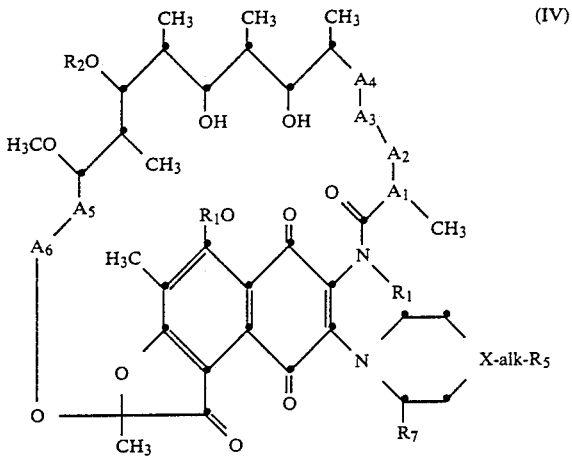

(IV)

and, if desired, converting a compound of formula I obtainable by the process or in another manner, or a salt thereof, into a different compound of the invention or a salt thereof, or converting a free compound of formula I obtainable by the process into a salt and/or a salt obtainable by the process into the free compound of formula I or into a different salt and, if desired, separating a mixture of isomers obtainable in accordance with the process.

Salts of the starting materials of formulae IIa and III that contain an acid phenolic hydroxy group are corresponding salts with bases of the kind indicated hereinbefore, whereas starting compounds of formula IIb that have one or two basic centres can form corresponding acid addition salts similar to the acid addition salts of formula I.

Reactive esterified hydroxy, for example Z, is especially hydroxy esterified with a strong inorganic acid or organic sulfonic acid, and is, for example, halogen, such as chlorine, bromine or iodine, sulfonyloxy, such as hydroxysulfonyloxy, halosulfonyloxy, for example fluorosulfonyloxy, $C_1-C_7$alkanesulfonyloxy that is unsubstituted or sulfonyloxy or trifluoromethanesulfonyloxy, $C_5-C_7$cycloalkanesulfonyloxy, for example cyclohexanesulfonyloxy, or benzenesulfonyloxy that is unsubstituted or substituted, for example, by $C_1-C_7$alkyl or halogen, for example p-bromobenzenesulfonyloxy or p-toluenesulfonyloxy.

The reactions described hereinbefore and hereinafter in the variants are carried out in a manner known per se, for example in the absence or, normally, in the presence, of a suitable solvent or diluent or a mixture thereof, the process being carried out, as required, with cooling, at room temperature or with heating, for example in a temperature range of approximately from $-80°$ to the boiling temperature of the reaction medium, preferably from about $-10°$ to about $+180°$ C. and, if necessary, in a closed vessel, under pressure, in an inert gas atmosphere and/or under anhydrous conditions.

Variant (a)

Z is preferably halogen, such as chlorine, bromine or iodine, as well as sulfonyloxy, such as methanesulfonyloxy or p-toluenesulfonyloxy.

The reaction is conducted in a manner known per se, advantageously in the presence of a base.

Suitable bases are preferably non-nucleophilic tertiary amines, for example tri-lower alkylamines, basic heterocycles and carbocyclic amines, such as ethyl diisopropylamine, triethylamine, pyridine, 1,5-diazabicyclo[4.3.0]non-5-ene (DBN), as well as 1,8-diazabicyclo[5.4.0]undec-7-ene (DBU).

The starting material of formula IIa can be prepared in a manner known per se, for example by the reaction of 3-halorifamycin S with piperazine protected in position 4 (for example analogously to U.S. Pat. No. 4,005,077), subsequent acylation to corresponding 1-O-acyl- or 1,8-di-O-acyl-rifamycin SV derivatives, and cyclisation in accordance with Variant (b). Finally, the protecting group is removed.

Variant (b)

$R_{1'}$ and $R_{1''}$ are each acyl, espec

The cyclisation of compounds of formula III is advantageously carried out with heating, for example in a temperature range of approximately from 50° to the boiling temperature of the reaction system, for example up to approximately 180° C., such as in a temperature range of from approximately 100° to approximately 170° C.

The cyclisation of compounds of formula III for example in which the structural elements $—A_1-A_2—$, $—A_3-A_4—$ and $—A_5-A_6—$ are each ethylene, can of course also be carried out at room temperature.

The starting material of formula III can be prepared, for example, by reacting rifamycin S or 3-halo-rifamycin S, especially 3-bromo-rifamycin S, with an amine of formula

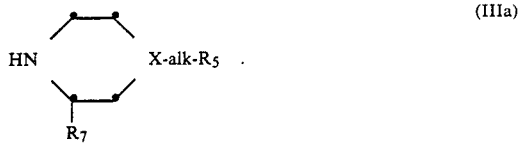

(IIIa)

The reaction is carried out especially with an excess of the amine of formula IIIa, for example in a temperature range of from about 0° to about 100° C., a mixture of the quinone and hydroquinone form being formed. This mixture can be converted into the corresponding hydroquinone ($R_1=$ H) (derivative of rifamycin SV) by reduction, for example by catalytic hydrogenation. By treatment with corresponding acylating agents, for example with an acid anhydride, such as pivaloyl chloride, in the presence of a base, such as pyridine, compounds of formula III in which $R_{1'}$ is acyl and $R_{1''}$ is hydrogen or $R_{1'}$ and $R_{1''}$ are acyl can be obtained. If the structural elements $—A_1-A_2—$, $—A_3-A_4—$ and $—A_5-A_6—$ are each vinylene, such compounds can be converted (also at the precursor stage), for example by catalytic hydrogenation, in each case depending on the choice of reducing agents and take up of the $H_2$ equivalents, into the corresponding tetrahydro form ($—A_1-A_2—$ and $—A_3-A_4—$ are each ethylene and $A_5-A_6$ is vinylene) or hexahydro form ($—A_1-A_2—$ and $-A_3-A_4A—$ and $—A_5-A_6—$ are each ethylene).

Variant (c)

The cyclisation is carried out especially by heating or irradiating the starting material.

The reaction is preferably carried out in an organic solvent, for example an alcohol, such as methanol, ethanol or isopropanol, a ketone, such as acetone or methyl ethyl ketone, a chlorinated hydrocarbon, such as chloroform or trichloroethane, an ether, such as diethyl ether, a base, such as pyridine or triethylamine, or a nitrile, such as acetonitrile. Preferred solvents are isopropanol or pyridine.

If the reaction temperature is too low, the reaction proceeds very slowly, but at too high a temperature a considerable proportion of undesired side-products are produced. A suitable temperature range is, for example, from about 50° to about 90° C., the temperature preferably being about 75° C.

The irradiation is carried out in a manner known per se, for example using conventional radiation sources, such as microwave radiation.

The resulting product can be purified and isolated, for example by chromatography and/or recrystallisation from a suitable solvent, such as petroleum ether.

The starting material of formula IV can be prepared in a manner known per se, for example by treating a compound of formula

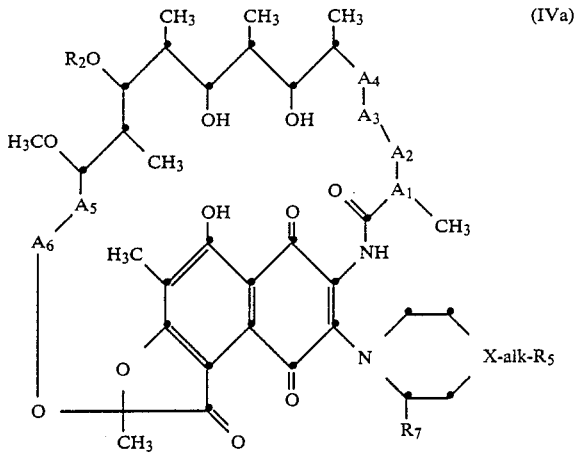

(IVa)

with an acylating agent with which the triacetyl group can be introduced into positions 8 and 14, such as pivaloyl chloride.

The invention relates also to the novel compounds obtainable in accordance with the above Process Variants.

A compound of formula I obtainable in accordance with the invention or in another manner, or a salt thereof, can be converted in a manner known oer se into a different compound of formula I.

Compounds of formula I in which the structural elements —$A_1$-$A_2$—, —$A_3$-$A_4$— and —$A_5$-$A_6$— are each vinylene, or —$A_1$-$A_2$— and —$A_3$-$A_4$— are each ethylene and —$A_5$-$A_6$— is vinylene, can be converted by reduction, for example by catalytic hydrogenation, into the corresponding tetrahydro (—$A_1$-$A_2$— and —$A_3$-$A_4$— are each ethylene and —$A_5$-$A_6$— is vinylene) or the corresponding hexahydro derivatives (—$A_1$-$A_2$—, —$A_3$-$A_4$— and —$A_5$-$A_6$— are each ethylene). The hydrogenation of the multiple bonds is, for example, carried out in the presence of hydrogenation catalysts, there being suitable for this purpose, for example, noble metals or derivatives thereof, for example oxides, such as nickel, Raney nickel, palladium, platinum oxide, which if appropriate can be carried on a substrate, for example on carbon or calcium carbonate. For homogeneous catalysis, the catalysts used are especially also complex rhodium compounds, for example tris-(triphenylphosphine)-rhodium(I) chloride. The hydrogenation may be carried out especially at pressures of from 1 to approximately 100 at. The corresponding hexahydro derivatives can be further hydrogenated by catalytic hydrogenation to form octahydro derivatives of formula I in which $R_3$ and $R_4$ are each hydrogen. If $R_3$ and $R_4$ together are a bond, this double bond can also be hydrogenated selectively in the presence of further double bonds in the Ansa ring using a suitable hydride, especially sodium borohydride. The reaction conditions may be so selected that first of all 16,17,18,19-tetrahydro derivatives are obtained (catalyst, for example Pd/C) and from these, or from correspondingly unsaturated starting materials, the 16,17,18,19,28,29-hexahydro compounds can be obtained directly and then converted to the corresponding octahydro derivatives by the absorption of a further $H_2$ equivalent (catalyst, for example, $PtO_2$) Irrespective of the degree of hydrogenation of the structural elements —$A_1$-$A_2$—, —$A_3$-$A_4$—, —$A_5$-$A_6$— it is possible for compounds of formula I in which $R_3$ and $R_4$ together are a bond to be hydrogenated selectively to compounds of formula I in which $R_3$ and $R_4$ are each hydrogen, for example by using a suitable hydride, especially $NaBH_4$.

It is also possible for unsaturated (cyclo-)aliphatic hydrocarbon radicals (alk or $R_5$) to be hydrogenated simultaneously during the hydrogenation reaction. In order to avoid undesirable side reactions, it is advantageous to use correspondingly hydrogenated compounds of formula IIa as starting materials and proceed in accordance with Variant (a).

If alk and the cycloaliphatic hydrocarbon radical $R_5$ in compounds of formula (I) are unsaturated hydrocarbon radicals, the multiple bonds can be saturated in a manner known per se. The hydrogenation of multiple bonds is effected, for example, by catalytic hydrogenation in the presence of hydrogenation catalysts, there being suitable for this purpose, for example, noble metals and derivatives thereof, for example oxides, such as nickel, Raney nickel, palladium, platinum oxide, which may, if desired, be carried on a substrate, for example carbon or calcium carbonate. The hydrogenation can be carried out preferably at pressures of from 1 to approximately 100 at.

Compounds of formula I in which $R_1$ is hydrogen can be acylated in a manner known per se, for example by reaction with the appropriate carboxylic acid or a reactive derivative thereof. Such reactive derivatives are, for example, anhydrides, including mixed anhydrides, such as an acid halide, for example an acid chloride, or anhydrides with a formic acid ester, an activated carboxylic acid ester, such as cyanomethyl ester, (4-)nitrophenyl ester, or a polyhalophenyl ester, for example pentachlorophenyl ester. The reaction with the carboxylic acid or a salt thereof is advantageously carried out with removal of water, for example azeotropic removal of the water of reaction, or by treatment with a suitable condensing agent, for example N,N'-dicyclohexylcarbodiimide. The reaction with a reactive acid derivative is advantageously carried out in the presence of a base. Similarly, the acetyl radical $R_2$ can be introduced into compounds of formula I in which $R_2$ is hydrogen by treatment with a suitable acetylating agent.

The acetyl radical $R_2$ and the acyl radical $R_1$ can be replaced by hydrogen by treatment with strong bases, such as alkali metal hydroxides. The acyl radical $R_1$ can also be removed selectively in the presence of the acetyl radical $R_2$, for example by treatment with a fluoride, such as an alkali metal fluoride, for example sodium or caesium fluoride, or with an ammonium fluoride, for example tetrabutylammonium fluoride.

Salts of compounds of formula (I) can be prepared in a manner known per se. Thus, for example, acid addition salts of compounds of formula (I) are obtained by treatment with an acid or with a suitable ion exchange reagent. Salts can be converted in customary manner into the free compounds; acid addition salts, for example, by treatment with a suitable basic agent.

Depending on the procedure and on the reaction conditions, the compounds of the invention having salt-forming, especially basic, properties, can be obtained in free form or, preferably, in the form of salts.

Owing to the close relationship between the novel compounds in free form and in the form of their salts, hereinbefore and hereinafter references to free compounds or their salts shall also, where appropriate with regard to context, include the corresponding salts or free compounds respectively.

The novel compounds, including the salts in the case of salt-forming compounds thereof, can also be obtained in the form of hydrates or include other solvents used for crystallisation.

Depending on the choice of starting materials and procedures, the novel compounds may be in the form of one of the possible isomers or in the form of mixtures thereof, for example depending on the number of asymmetric carbon atoms they may be in the form of pure optical isomers, such as antipodes, or in the form of mixtures of isomers, such as racemates, mixtures of diastereoisomers or mixtures of racemates.

Resulting mixtures of racemates can be separated in known manner into the pure isomers or racemates on the basis of the physico-chemical differences between the components, for example by fractional crystallisation.

Resulting racemates can also be resolved into the optical antipodes by known methods, for example by recrystallisation from an optically active solvent, chromatography on chiral adsorbents, with the aid of suitable microorganisms, by cleavage with specific immobilised enzymes, via the formation of inclusion compounds, for example using chiral Crown ethers, only one enantiomer being complexed, or by conversion into diastereoisomeric salts, for example by reaction of a basic end product racemate with an optically active acid, such as a carboxylic acid, for example tartaric or malic acid, or a sulfonic acid, for example camphorsulfonic acid, and separation of the resulting mixture of diastereoisomers, for example on the basis of their different solubilities, into the diastereoisomers from which the desired enantiomer can be freed by the action of suitable agents. It is advantageous to isolate the more active enantiomer. When the $C_{16}$-$C_{17}$— and $C_{18}$-$C_{19}$-double bonds (—$A_1$-$A_2$— and —$A_3$-$A_4$—=ethylene) are hydrogenated an additional asymmetrically substituted C-atom (C-16) results. Accordingly there exist in addition two different stereoisomeric arrangements at the C-16 atom, the R- and S-configuration, respectively, according to the Cahn-Ingold-Prelog nomenclature system. The hydrogenation of the 1-deoxy-15-deoxo1,15-oxy-rifamycins proceeds practically stereospecifically with respect to C-16. To obtain the other stereoisomeric form with respect to C-16, it is necessary, for example, to start from corresponding hydro derivatives of formula III in which $R_1'$ and $R_1''$ are hydrogen, to separate the stereoisomeric forms concerned, for example by conventional chromatographic methods, and then to acylate accordingly the so-obtainable compounds of formula III and carry out the cyclisation, for example in accordance with Variant (b).

On the basis of the investigations in the test procedure described at the beginning for determining the lipid-lowering properties of the compounds of the invention, it was ascertained that one of the two possible stereoisomeric arrangements with respect to C-16 is responsible for an especially high degree of inhibition of the level of cholesterol. It has not until now been possible to ascertain the absolute configuration at C-16 for these stereoisomers.

Accordingly, the present invention relates especially to the compounds of formula I described at the beginning and in the Examples, and the salts thereof, in which there is such a stereoisomeric arrangement at C-16.

The invention also relates to those embodiments of the process in which a compound obtainable as intermediate at any stage of the process is used as starting material and the remaining steps are carried out, or a starting material is used in the form of a derivative or salt and/or its diastereoisomers, racemates or antipodes or, especially, is formed under the reaction conditions.

The reaction product is isolated from the reaction mixture obtainable in accordance with the process and worked up in a manner known per se, for example by dilution with water, and/or optionally by neutralisation or slight acidification (up to approximately pH 3) with an aqueous acid, such as an inorganic or organic acid, for example a mineral acid or, advantageously, citric acid, and addition of a water-immiscible solvent, such as a chlorinated hydrocarbon, for example chloroform or methYlene chloride, the reaction product changing into the organic phase from which it can be obtained in purified form in conventional manner, for example by drying, concentration of the solvent by evaporation, and crystallisation and/or chromatography of the residue, or by other conventional purification methods. If the above reaction results, for example, in a mixture of acylated compounds or diastereoisomeric forms, this can be resolved in a manner known oer se, for example by means of fractional crystallisation, chromatography etc. into the desired individual acyl compounds or diastereoisomeric forms, respectively.

In the process of this invention it is preferred to use those starting materials that lead to the compounds referred to at the outset as being especially valuable. The invention further relates to novel starting materials that have been specially developed for the preparation of the compounds of the invention, especially novel compounds of formula III, their use, and processes for their prepara tion, the variables $A_1$-$A_2$, $A_3$-$A_4$, $A_5$-$A_6$, $R_1$, $R_2$, $R_3$, $R_4$, $R_5$, $R_6$, $R_7$, X and alk having the meanings given for the respective preferred compound groups of formula I. The present inVention also relates to the use of compounds of formula I and salts thereof alone or together with adjuncts, as well as in combination with other active substances, as agents for the therapeutic treatment, that is curative as well as preventive treatment, of diseases or pathological conditions that are indicated or caused, for example, by an increased content of chlolesterol and/or triglycerides in blood, especially in blood serum. The active ingredients of the invention are administered to the warm-blooded animals requiring treatment, primarily humans, in therapeutically effective amounts, preferably in the form of pharmaceutical compositions together with conventional pharmaceutical carriers and/or adjuncts. Depending on the species, body weight, age and individual condition, for example daily doses of about 1 to about 100, preferably of about 3 to about 50, mg/kg of body weight, which doses may be exceeded in acute cases, are administered to warm-blooded animals. The invention also relates by analogy to the corresponding method of medical treatment.

The invention further relates to pharmaceutical preparations that contain the compounds of the invention or pharmaceutically acceptable salts thereof as active ingredients, and to processes for the preparation thereof.

The pharmaceutical preparations of the invention, which contain the compound of the invention or pharmaceutically acceptable salts thereof, are for enteral, such as oral or also rectal, and parenteral administration to warm-blooded animals, and contain the pharmacological active ingredient on its own or together with a pharmaceutically acceptable carrier. The daily dose of the active ingredient depends on age and individual condition and also on the mode of administration. The novel pharmaceutical preparations contain, for example, from about 10% to about 80%, preferably from about 20% to about 60%, of the active ingredient. Pharmaceutical preparations of the invention for enteral or parenteral administration are, for example, those in dosage unit forms, such as dragées, tablets, capsules or suppositories, as well as ampoules. These pharmaceutical preparations are prepared in a manner known oer se, for example by conventional mixing, granulating, confectioning, dissolving or lyophilising methods. For example, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, maize, wheat, rice or potato starch, gelatin, tragacanth, methylcellulose, and/or polyvinylpyrrolidone, if desired disintegrators, such as the above-mentioned starches, also carboxymethyl starch, crosslinked polyvinylpyrrolidone, agar, or alginic acid or a salt thereof, such as sodium alginate. Adjuncts are especially solvents, flow-regulating agents and lubricants, for example silicic acid, talc, stearic acid or salts thereof, such as magnesium or calcium stearate, and/or polyethylene glycol. Dragée cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or dragée coatings, for example for the purposes of identification or to indicate different doses of active ingredient.

Other orally administrable pharmaceutical preparations are dry-fill capsules made of gelatin, and also soft, sealed capsules made of gelatin and a plasticiser, such as glycerol or sorbitol. The dry-fill capsules may contain the active ingredient in the form of a granulate, for example in a mixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules that contain a combination of the active ingredient with a base material. Suitable base materials are, for example, liquid triglycerides, polyethylene glycols or paraffin hydrocarbons.

There are suitable for parenteral administration especially aqueous solutions of an active ingredient in water-soluble form, for example a water-soluble salt, and also suspensions of the active ingredient, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions that contain viscosity-increasing substances, for example sodium carboxymethylcellulose, sorbitol and/or dextran, and, where appropriate, also stabilisers.

The dosage of the active ingredient depends on the species of warm-blooded animal, the age and individual condition, as well as on the mode of administration. Normally, in the case of oral administration an approximate daily dose of about 150 mg to about 1500 mg, advantageously in several equal partial doses, will be administered to a warm-blooded animal weighing about 75 kg.

The following Examples illustrate the above-described invention, but in no way limit the scope thereof. Temperatures are in degrees Celsius. The NMR spectra were advantageously taken at elevated temperatures, especially at about 80° C., in DMSO; the chemical shifts of the signals are given in ppm.

The chemical name of the basic structure from which the rifamycin derivatives of the present invention are derived is as follows: 1-deoxy-15-deoxo-1,15-oxy-rifamycin, and the associated structural formula may be illustrated as follows:

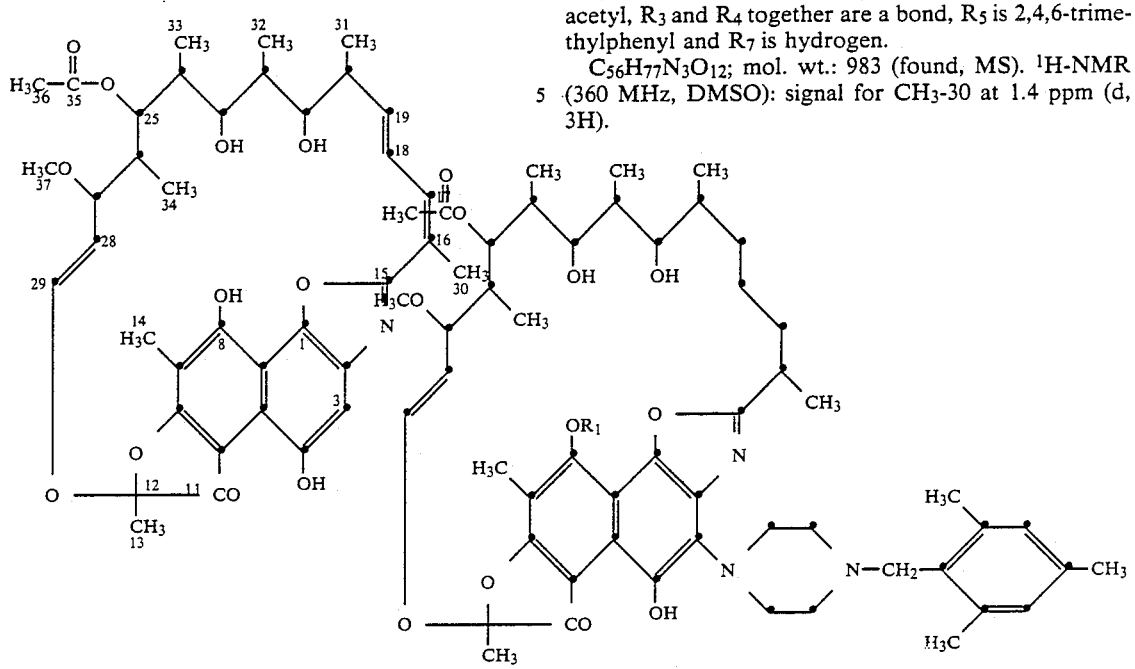

EXAMPLE 1

A solution of 2 g of 8-O-pivaloyl-1-deoxy-15-deoxo-1,15-oxy-3-[4-(2,4,6-trimethylbenzyl)-piperazin-1-yl]-rifamycin of formula I in which the structural elements —$A_1$-$A_2$—, —$A_3$-$A_4$— and —$A_5$-$A_6$— are each vinylene, X is >N—, alk is methylene, $R_1$ is pivaloyl, $R_2$ is acetyl, $R_3$ and $R_4$ together are a bond and $R_5$ is 2,4,6-trimethylphenyl and $R_7$ is hydrogen is hydrogenated in 100 ml of ethanol in the presence of 0.2 g of palladium on carbon (10%) at 25° and normal pressure until the absorption of hydrogen is complete. The catalyst is then removed by filtration and the solvent is concentrated by evaporation under vacuum. The dark red residue is chromatographed on 200 g of silica gel with the eluant petroleum ether/ethyl acetate (3:1). Two rapidly migrating red-coloured bands, followed by one strong red main band, are observed. The eluate of this red main band is collected and concentrated by evaporation. The residue consists of epimerically pure 16,17,18,19-tetrahydro-8-O-pivaloyl-1-deoxy-15-deoxo-1,15-oxy-3-[4-2,4,6-trimethylbenzyl)-piperazin-1-yl]-rifamycin of formula I in which the structural elements —$A_1$-$A_2$— and —$A_3$-$A_4$— are each ethylene and —$A_5$-$A_6$— is ethylene, X is >N—, alk is methylene, $R_1$ is pivaloyl, $R_2$ is acetyl, $R_3$ and $R_4$ together are a bond, $R_5$ is 2,4,6-trimethylphenyl and $R_7$ is hydrogen.

$C_{56}H_{77}N_3O_{12}$; mol. wt.: 983 (found, MS). $^1$H-NMR (360 MHz, DMSO): signal for $CH_3$-30 at 1.4 ppm (d, 3H).

The starting material can be prepared as follows: A mixture of 5 g of 3-[4-(2,4,6-trimethylbenzyl)-piperazin1-yl]-rifamycin SV [cf. EP 244 398, Example 2; the preparation of other rifamycin SV compounds used in the following Examples is described, for example, in U.S. Pat. No. 4,005,077], 50 ml of dry pyridine and 4.5 ml of pivaloyl chloride is kept at 50° C. for 30 minutes. The solvent is the removed by evaporation under vacuum. The oily residue is dissolved in ethyl acetate and the solution is washed with 2N hydrochloric acid, with a buffer solution of pH 7, and with a solution of sodium chloride. The whole is dried over sodium sulfate and concentrated by evaporation and the yellow residue is crystallised from ether/hexane, yielding 1,8-di-O-pivaloyl-3-[4-(2,4,6-trimethylbenzyl)-piperazin-1yl]-rifamycin SV with a melting point of 203°–204° C. $C_{61}H_{83}N_3O_{14}$; mol. wt.: 1081 (found, MS)

The 1,8-di-O-pivaloyl compounds used in the following Examples can be prepared in an analogous manner.

30 g of 1,8-di-O-pivaloyl-3-[4-(2,4,6-trimethylbenzyl)-piperazin-1-yl]-rifamycin SV are dissolved with the application of heat in 1000 ml of 2-methoxyethanol and refluxed under nitrogen for 5 hours. The solvent is then concentrated by evaporation in vacuo and the residue is crystallised twice from methanol. 8-O-pivaloyl-1-deoxy-15-deoxo-1,15-oxy-3-[4-(2,4,6-trimethylbenzyl)-piperazin-1-yl]-rifamycin of formula I in which the structural elements —$A_1$-$A_2$—, —$A_3$-$A_4$— and —$A_5$-$A_6$— are each vinylene, X is >N—, alk is methylene, $R_1$ is pivaloyl, $R_2$ is acetyl, $R_3$ and $R_4$ together are a bond, $R_5$ is 2,4,6-trimethylphenyl and $R_7$ is hydrogen, is obtained. M.p. 160°–165° (crystallisation from ethanol). $C_{56}H_{73}N_3O_{12}$; M=979, found (MS): 979; $^1$H-NMR (360 MHz, CDCl$_3$, TMS): 1.49 (s, 9H, pivaloyl at O-8).

EXAMPLE 2

A solution of 10 g of the target product of Example 1 in 800 ml of ethanol is hydrogenated for 1 hour in the presence of 1.2 g of sulfuric acid and 1 g of $PtO_2$ at 25°

C. and normal pressure. After that time 1 equivalent of hydrogen (230 ml) has been taken up. The catalyst is removed by filtration, the filtrate is neutralised by the addition of aqueous sodium bicarbonate solution, a saturated solution of sodium chloride is added and the hydrogenation product is extracted by repeated shaking with ethyl acetate. After drying and concentrating the ethyl acetate extract by evaporation, the residue is purified by chromatography in the manner described in Example 1. The red material obtained in the strong main band is epimerically pure 16,17,18,19,28,29-hexahydro-8-O-pivaloyl-1-deoxy-15-deoxo-1,15-oxy-3-[4-(2,4,6-trimethylbenzyl)-pipeazin-1-yl]-rifamycin of formula I in which the structural elements —$A_1$–$A_2$—, —$A_3$–$A_4$— and —$A_5$–$A_6$— are each ethylene, X is >N—, alk is methylene, $R_1$ is pivaloyl, $R_2$ is acetyl, $R_3$ and $R_4$ together are a bond, $R_5$ is 2,4,6-trimethylphenyl and $R_7$ is hydrogen. $C_{56}H_{79}N_3O_{hd\ 12}$; mol. wt.: 985 (found, MS, FD). $^1$H-NMR (360 MHz, DMSO): all signals of vinylic protons have disappeared.

ene, X is >N—, alk is methylene, $R_1$ is pivaloyl, $R_2$ is acetyl, $R_3$ and $R_4$ together are a bond, $R_5$ is 2,4,6-trimethylphenyl and $R_7$ is hydrogen are dissolved in 500 ml of ethanol and hydrogenated in the presence of 0.5 g of $PtO_2$ and 0.7 g of sulfuric acid at room temperature and normal pressure until 4 equivalents of hydrogen (~460 ml) have been taken up. The catalyst is removed by filtration, the filtrate is neutralised by aqueous sodium bicarbonate solution, a saturated solution of sodium chloride is added and the hydrogenation product is extracted by repeated shaking with ethyl acetate. After drying and concentrating the ethyl acetate extract by evaporation, the residue is dissolved in ether. After standing for some time, 16,17,18,19,28,29-hexahydro-8O-pivaloyl-1-deoxy-11,15-deoxo-1,15-oxy-11-hydroxy-3-[4-(2,4,6-trimethylbenzyl)-piperazin-1yl]rifamycin of formula I in which the structural elements —$A_1$–$A_2$—, -$A_3$-$A_4$ and —$A_5$–$A_6$— are each ethylene, X is >N—, alk is methylene, $R_1$ is pivaloyl, $R_2$ is acetyl, $R_3$ and $R_4$ are each hydrogen, $R_5$ is 2,4,6-trimethyphe-

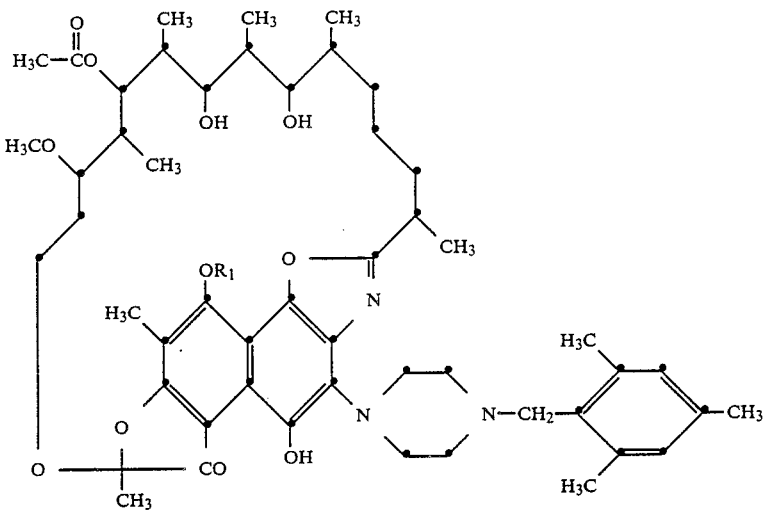

EXAMPLE 3

In a manner analogous, for example, to that described in Example 2, 5 g of 8-O-pivaloyl-1-deoxy-15-deoxo-1,15-oxy-3-[4-(2,4,6-trimethylbenzyl)-piperazin-1yl]-rifamycin of formula I in which the structural elements —$A_1$–$A_2$—, —$A_3$–$A_4$— and —$A_5$–$A_6$— are each vinylnyl and $R_7$ is hydrogen crystalises. The faintly brown-red crystals, which after recrystallisation from ether form colourless platelets, melt at 226°–227° C. (decomposition). $C_{56}H_{81}N_3O_{12}$; mol. wt.: 987 (found, MS, FD).

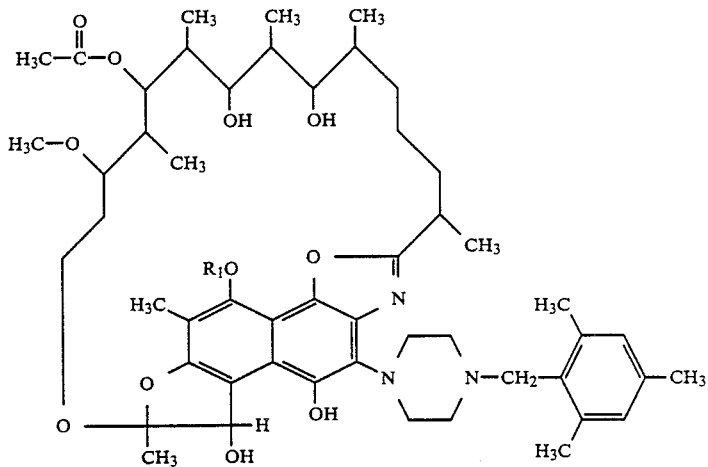

EXAMPLE 4

In a manner analogous, for example, to that described in Example 1 in the manufacture of the starting material, there is obtained from 1,8-di-O-pivaloyl-3-[4-(1-naphthyl-methyl)-piperazin-1-yl]-rifamycin SV by heating for 5 hours in 2-methoxyethanol, 8-O-pivaloyl-1-deoxy-15-deoxo-1,15-oxy-3-[4-(1-naphthyl-methyl)-piperazine-1yl]-rifamycin of formula I in which the structural elements —$A_1$-$A_2$—, —$A_3$-$A_4$— and —$A_5$-$A_6$— are each vinylene, X is >N—, alk is methylene, $R_1$ is pivaloyl, $R_2$ is acetyl, $R_3$ and $R_4$ together are a bond, $R_5$ is 1-naphthyl and $R_7$ is hydrogen, which crystallises from methanol/water in the form of red crystals. M.p. 207°. $C_{57}H_{69}N_3O_{12}$; mol. wt.: 987 (found, MS, FD).

nylene, X is >N—, alk is 2-methyl-1,3-propylene, $R_1$ is pivaloyl, $R_2$ is acetyl, $R_3$ and $R_4$ together are a bond, and $R_5$ and $R_7$ are hydrogen, having a melting point of 187°–188° (crystallised from methanol/-water). $C_{56}H_{69}N_3O_{12}$; mol. wt.: 903 (found, MS, FD). $^1$H-NMR (360 MHz, CDCl$_3$): signals of the isobutyl group at 0.92 (6H, (CH$_3$)$_2$CH); 2.16 (d, 2H, CH$_2$N).

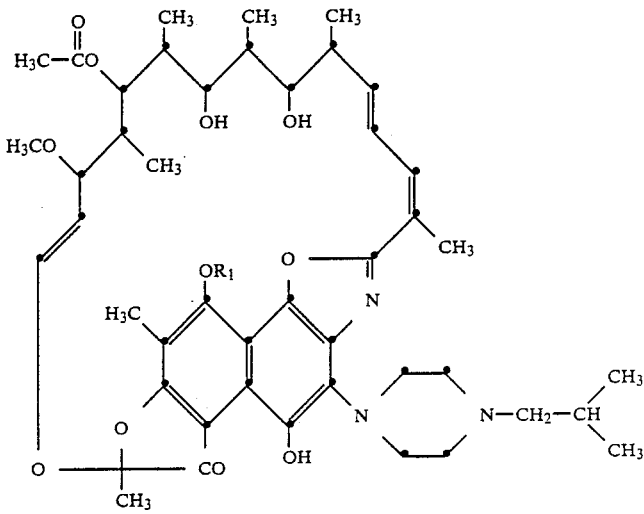

EXAMPLE 6

In a manner analogous, for example, to that described in Example 3, hydrogenation of 8-O-pivaloyl-1-deoxy-15-deoxo-1,15-oxy-3-(4-isobutyl-1-piperazinyl)rifamycin of formula I in which the structural elements —$A_1$-$A_2$—, —$A_3$-$A_4$— and —$A_5$-$A_6$— are each vinylene, X is >N—, alk is 2-methyl-1,3-propylene, $R_1$ is pivaloyl, $R_2$ is acetyl, $R_3$ and $R_4$ together are a bond, and $R_5$ and $R_7$ are hydrogen, with PtO$_2$ in ethanol with the addition of sulfuric acid, yields 16,17,18,19,28,29-hexahydro-8O-pivaloyl-1-deoxy-11,15-deoxo-1,15-oxy-11-hydroxy-3-[4-(2,4,6-trimethylbenzyl)-piperazin-1yl]-rifamycin of formula I in which the structural elements —$A_1$-$A_2$—, —$A_3$-$A_4$— and —$A_5$-$A_6$— are each ethyl-

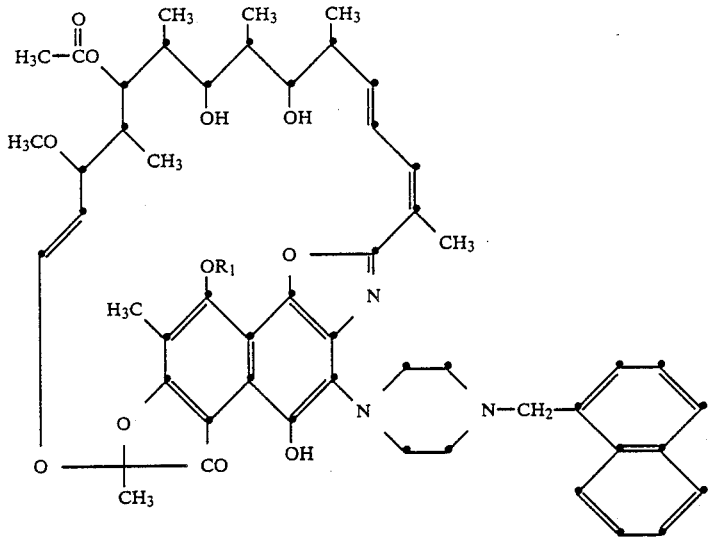

EXAMPLE 5

In a manner analogous, for example, to that described in Example 1 in the manufacture of the starting material, there is obtained from 1,8-di-O-pivaloyl-3-(4-isobutyl-1-piperazinyl)-rifamycin SV, 8-O-pivaloyl-1-deoxy-15-deoxo-1,15-oxy-3-(4-isobutyl-1-piperazinyl)-rifamycin of formula I in which the structural elements —$A_1$-$A_2$—, —$A_3$-$A_4$and and —$A_5$-$A_6$— are each viene, X is >N—, $R_1$ is pivaloyl, $R_2$ is acetyl, $R_3$ and $R_4$ are each hydrogen, $R_5$ and $R_7$ are hydrogen, and alk is 2-methyl-1,3-propylene. Recrystallisation of the faintly reddish coloured crystals from hexane yields colourless square platelets melting at from 150° to 160° C. $C_{50}H_{77}N_2O_{12}$; mol. wt.: 911 (found, MS, FD).

EXAMPLE 7

In a manner analogous, for example, to that described in Example 1 in the manufacture of the starting material, there is obtained from 1,8-di-O-pivaloyl-3-[4-(4-phenylbenzyl)-1-piperazinyl]-rifamycin SV by heating for 5 hours in 2-methoxyethanol under nitrogen, 8-O-pivaloyl-1-deoxy-15-deoxo-1,15-oxy-3-[4-(4-phenbenzyl)-1-piperazinyl]-rifamycin of formula I in which the structural elements —$A_1$-$A_2$—, —$A_3$-$A_4$— and —$A_5$-$A_6$— are each vinylene, X is >N—, alk is methylene, $R_1$ is pivaloyl, $R_2$ is acetyl, $R_3$ and $R_4$ together are a bond, $R_5$ is 4-biphenylyl and $R_7$ is hydrogen. The compound crystallises from hexane/ether in the form of red crystals that melt from 140°. $C_{59}H_{71}N_2O_{12}$; mol. wt.: 1013 (found, MS, FAB).

EXAMPLE 8

A 5% methanolic solution of $NaBH_4$ is added dropwise to a solution in 20 ml of methanol, of 1 g of 16,17,18,19-tetrahydro-8-O-pivaloyl-1-deoxy-15-deoxo-1,15-oxy-3-[4-(2,4,6-trimethylbenzyl)-1-piperazinyl)-rifamycin of formula I in which the structural elements —$A_1$-$A_2$—, —$A_3$-$A_4$— are each ethylene and —$A_5$-$A_6$— is vinylene, X is >N—, alk is methylene, $R_1$ is pivaloyl, $R_2$ is acetyl, $R_3$ and $R_4$ together are a bond, $R_5$ is 2,4,6-trimethylphenyl and $R_7$ is hydrogen, until the reaction solution has lost its red colour. The reaction solution is then acidified with aqueous ascorbic acid, saturated NaCl solution is added, and the reaction product is taken up with ethyl acetate. After washing the ethyl acetate extract with buffer solution pH 7, drying over $Na_2SO_4$, and concentrating the ethyl acetate extract by evaporation, 16,17,18,19-tetrahydro-8O-pivaloyl-1-deoxy-11,15-deoxo-1,15-oxy-11-hydroxy-3-[4-(2,4,6-trimethyl-benzyl)-1-piperazinyl]-rifamycin of formula I is obtained in which the structural elements —$A_1$-$A_2$— and —$A_3$-$A_4$— are each ethylene and —$A_5$-$A_6$— is vinylene, alk is methylene, $R_1$ is pivaloyl, $R_2$ is acetyl, $R_3$, $R_4$ and $R_7$ are each hydrogen and $R_5$ is 2,4,6-trimethylphenyl. $C_{56}H_{79}N_2O_{12}$; mol. wt.: 985 (found, MS, FD). $^1$H-NMR (360 MHz, DMSO): 5.10 (dd, 1H, H-28) +6.39 (d, 1H, H-29) [only 2 signals of vinylic protons left]; 5.79 (s, 1H, H-15); 1.39 (d over m, at least 3H, $CH_3$-30).

EXAMPLE 9

0.2 g of solid $NaBH_4$ is added, with stirring, to a solution, in 100 ml of tetrahydrofuran and 100 ml of methanol, of 5 g of 8-O-pivaloyl-1-deoxy-15-deoxo-1,15-oxy-3-[4-(2,4,6-trimethylbenzyl)-1-piperazinyl)-rifamycin of formula I in which the structural elements —$A_1$-$A_2$—, —$A_3$-$A_4$ and —$A_5$-$A_6$— are each vinylene, X is >N—, alk is methylene, $R_1$ is pivaloyl, $R_2$ is acetyl, $R_3$ and $R_4$ together are a bond, $R_5$ is 2,4,6-trimethylphenyl and $R_7$ is hydrogen. After 10 minutes, the pale-yellow reaction solution is acidified with aqueous ascorbic acid solution, and water and saturated aqueous NaCl solution are added. The reaction mixture is taken up with ethyl acetate, and the extract is washed with buffer solution of pH 7, dried over $Na_2SO_4$ and concentrated by evaporation. The oily residue crystalilises from ether/pentane, yielding 8-O-pivaloyl-1-deoxy-11,15-deoxo-1,15-oxy-11-hydroxy-3-[4-(2,4,6-trimethylbenzyl)-1-piperazinyl)-rifamycin of formula I in which the structural elements —$A_1$-$A_2$—, —$A_3$-$A_4$— and —$A_5$-$A_6$— are each vinylene, X is >N—, alk is methylene, $R_1$ is pivaloyl, $R_2$ is acetyl, $R_3$, $R_4$ and $R_7$ are each hydrogen, and $R_5$ is 2,4,6-trimethylphenyl. The substance forms pale-yellowish crystals having a melting point of 205° C. $C_{56}H_{75}N_2O_{12}$; mol. wt.: 981 (found, MS, FD). 1H-NMR (360 MHz, CDCl$_3$, 50°): 5,78 (s, 1H, H-15).

EXAMPLE 10

In a manner analogous, for example, to that described in Example 1 in the manufacture of the starting material, there is obtained from 1,8-di-O-pivaloyl-3-[4(2,5-dimethylbenzyl)-1-piperazinyl]-rifamycin, 8-O-pivaloyl-1-deoxy-15-deoxo-1,15-oxy-3-[4-(2,5-dimethylbenzyl)-1piperazinyl]-rifamycin of formula I in which the structural elements —$A_1$-$A_2$—, —$A_3$-$A_4$— and —$A_5$-$A_6$— are each vinylene, X is 22 N—, alk is methylene, $R_1$ is pivaloyl, $R_2$ is acetyl, $R_3$ and $R_4$ together are a bond, $R_5$ is 2,5-dimethylphenyl and $R_7$ is hydrogen, m.p. 220° (crystallised from methanol). $C_{55}H_{71}N_2O_{12}$; mol. wt.: 965 (found, MS, DCI). $^1$H-NMR spectrum (360 MHz, DMSO-d$_6$): signals of the 2,5-dimethylbenzyl group at 3.48 (—$CH_2$—), 2.27 and 2.32 (arom. $CH_3$) as well as 7.09 (1 arom. H) and 7.0 (centr. AB, 2 arom. H) ppm.

EXAMPLE 11

In a manner analogous, for example, to that described in Example 1 in the manufacture of the starting material, there is obtained from 1,8-di-O-pivaloyl-3-(4-benzyl-1-piperazinyl)-rifamycin, 8-O-pivaloyl-1-deoxy-15-deoxo-1,15-oxy-3-(4-benzyl-1-piperazinyl)-rifamycin of formula I in which the structural elements —$A_1$-$A_2$—, —$A_3$-$A_4$— and —$A_5$-$A_6$— are each vinylene, X is >N—, $R_1$ is pivaloyl, $R_2$ is acetyl, $R_3$ and $R_4$ together are a bond, alk is methylene, $R_5$ is phenyl and $R_7$ is hydrogen. The compound crystallises from methanol/water in the form of thin crystalline platelets that melt at from 181°–182°. $C_{53}H_{67}N_2O_{12}$; mol. wt.: 937 (found, MS, FAB).

EXAMPLE 12

In a manner analogous, for example, to that described in Example 1 in the manufacture of the starting material, there is obtained from 1,8-di-O-pivaloyl-3-(4-cyclohexylmethyl-1-piperazinyl)-rifamycin, 8-O-pivaloyl-1-deoxy-15-deoxo-1,15-oxy-3-(4-cyclohexylmethyl-1-piperazinyl)-rifamycin of formula I in which the structural elements —$A_1$-$A_2$—, —$A_3$-$A_4$— and —$A_5$-$A_6$— are each vinylene, X is >N—, alk is methylene, $R_1$ is pivaloyl, $R_2$ is acetyl, $R_3$ and $R_4$ together are a bond, $R_5$ is cyclohexyl and $R_7$ is hydrogen. The compound crystallises from methanol in the form of platelets that melt at from 155°–156°. $C_{53}H_{73}N_3O_{12}$; mol. wt.: 943 (found, MS, DCI).

EXAMPLE 13

In a manner analogous, for example, to that described in Example 1 in the manufacture of the starting material, there is obtained from 1,8-di-O-pivaloyl-3-[4-(cyclohex-3-en-1-ylmethyl)-1-piperazinyl)-rifamycin SV, 8-O-pivaloyl-1-deoxy-15-deoxo-1,15-oxy-3-[4-(cyclohex-3-en-1-ylmethyl)-1-piperazinyl)-rifamycin of formula I in which the structural elements —$A_1$-$A_2$—, —$A_3$-$A_4$— and —$A_5$-$A_6$— are each vinylene, X is >N—, alk is methylene, $R_1$ is pivaloyl, $R_2$ is acetyl, $R_3$ and $R_4$ together are a bond, $R_5$ is cyclohex-3-en-1-yl and $R_7$ is hydrogen. The compound crystallises from methanol in the form of rhomboidal platelets, which with previous sintering melt at 165°. $C_{53}H_{71}N_2O_{12}$; mol. wt.: 941 (found, MS, DCI). $^1$H-NMR (360 MHz, DMSO-d$_6$): 5.66 (s, 2H, 2 olef. H in cyclohexene), 2.26 (t, >N—CH$_2$—CH<, overlayered with s at 2.24 of CH$_3$-30) ppm.

The starting material can be prepared as follows:

(a) 2 g of N-(cyclohex-3-en-1-ylmethyl)-piperazine are added to a solution of 5 g of 3-bromorifamycin S in 50 ml of tetrahydrofuran and left to stand for 30 minutes at 20°. The whole is then acidified by the addition of aqueous citric acid solution and the reaction product is taken up in ethyl acetate. Drying and concentration of the ethyl acetate extract by evaporation yields a dark residue. This is dissolved in methanol and aqueous ascorbic acid solution is added dropwise thereto. The solution turns yellow during the course of this and, after a short period, 3-[4-(cyclohex-3-en-1-ylmethyl)-piperazin-1-yl]-rifamycin SV precipitates in the form of yellow-coloured crystals that melt at 170°-172°.

(b) A mixture of 5 g of 3-[4-(cyclohex-3-en-1-ylmethyl)-piperazin-1-yl]-rifamycin SV, 50 ml of dry pyridine and 4.5 ml of pivaloyl chloride is heated at 50° for 30 minutes. The solvent is then evaporated in vacuo. The oily residue is dissolved in ethyl acetate and washed with 2N hydrochloric acid, with buffer solution of pH 7 and with a solution of sodium chloride. After drying and concentrating by evaporation, a yellow residue of crude 1,8-di-O-pivaloyl-3-[4-(cyclohex-3 en-1-ylmethyl)-1-piperazinyl-rifamycin SV is obtained, which is further processed without being further purified.

EXAMPLE 14

A methanolic solution of 8-O-pivaloyl-1-deoxy15-deoxo-1,15-oxy-3-[4-(2,4,6-trimethylbenzyl)-1-piperazinyl]-N,15,16,17,18,19,28,29-octahydrorifamycin of formula I in which the structural elements —$A_1$-$A_2$—, —$A_3$-$A_4$ and —$A_5$-$A_6$— are each ethylene, X is >N—, alk is methylene, $R_1$ is pivaloyl, $R_2$ is acetyl, $R_3$, $R_4$ and $R_7$ are each hydrogen and $R_5$ is 2,4,6-trimethylphenyl (target product of Example 3) is acidified with excess aqueous solution of L(+)-ascorbic acid, diluted with a large amount of water and extracted by shaking with ethyl acetate. In the course of this, the ascorbic acid salt of the octahydro derivative passes into the ethyl acetate phase. After drying over Na$_2$SO$_4$ and concentrating the ethyl acetate solution by evaporation, the ascorbate of 8-O-pivaloyl-1-deoxy-11,15-deoxo-1,15-oxy-11-hydroxy-3-[4-*2,4,6-trimethylbenzyl)-1-piperazinyl]-16,17,18,19,28,29-hexahydrorifamycin of formula I in which the structural elements —$A_1$-$A_2$—, —$A_3$-$A_4$— and —$A_5$-$A_6$— are each ethylene, X is >N—, alk is methylene, $R_1$ is pivaloyl, $R_2$ is acetyl, $R_3$, $R_4$ and $R_7$ are each hydrogen and $R_5$ is 2,4,6-trimethylphenyl remains, in the form of a colourless lacquer. On the addition of ether the compound crystallises from ethyl acetate in the form of long thin prisms that melt at approximately 200 with decomposition.

EXAMPLE 15

In a manner analogus, for example, to that described in Example 14, there is obtained from 8-O-pivaloyll-deoxy-11,15-deoxo-1,15-oxy-11-hydroxy-3[4-(2,4,6-trimethylbenzyl)-1-piperazinyl]-16,17,18,19-tetrahydrorifamycin SV (target product of Example 8) the ascorbic acid salt of the compound of formula I in which the structural elements —$A_1$-$A_2$— and —$A_3$-$A_4$— are each ethylene and —$A_5$-$A_6$— is vinylene, X is >N—, alk is methylene, $R_1$ is pivaloyl, $R_2$ is acetyl, $R_3$, $R_4$ and $R_7$ are each hydrogen and $R_5$ is 2,4,6trimethylphenyl. The salt forms colourless prisms having a melting point of 175° (decomposition).

EXAMPLE 16

10 ml of pivaloyl chloride are added dropwise, at 0°, with stirring, to a solution of 10 g of 16,17,18,19,28,29-hexahydro-3-[4-(2,4,6-trimethylbenzyl)-1-piperazinyl]-rifamycin (diastereoisomeric mixture) in 100 ml of pyridine and the reaction solution is left to stand at room temperature for 4 hours. Water is then added, the whole is acidified with dilute hydrochloric acid and the reaction product is taken up in ethyl acetate. The ethyl acetate extract is washed with dilute acid, with buffer solution of pH 7 and with a saturated solution of sodium chloride, then dried over Na$_2$SO$_4$ and concentrated by evaporation in vacuo. The residue contains the 2 diastereoisomeric, red-coloured hexahydro derivatives, which are separated by chromatography: when chromatography is repeated on 1 kg of silica gel with the eluant n-hexane/ethyl acetate 3:1, the more rapidly migrating of the 2 redcoloured bands in this system is isolated. It contains diastereoisomerically pure 16,17,18,19,28,29-hexahydro-8-O-pivaloyl-1-deoxy-15-deoxo-1,15-oxy-3-[4-2,4,6-trimethylbenzyl)-piperazin-1-yl]-rifamycin of formula I in which the structural elements —$A_1$-$A_2$—, —$A_3$-$A_4$— and —$A_5$-$A_6$— are each ethylene, X is >N—, alk is methylene, $R_1$ is pivaloyl, $R_2$ is acetyl, $R_3$ and $R_4$ together are a bond, $R_5$ is 2,4,6-trimethylphenyl and $R_7$ is hydrogen, which is diastereoisomeric to the target product of Example 2.

$C_{56}H_{79}N_2O_{12}$; mol. wt.: 985 (found, MS, FAB).

The starting material can be prepared, for example, as follows: 0.5 g of PtO$_2$ is added to a solution of 3 g of 3-[4-(2,4,6-trimethylbenzyl)-piperazin-rifamycin SV in 300 ml of ethanol, and the whole is hydrogenated for 13 hours at room temperature and under normal pressure. The catalyst is then filtered off through a layer of kieselguhr, the filtrate is concentrated to dryness by evaporation, and the residue is crystallised in a mixture of ethyl acetate and diethyl ether, yielding 3-[4-(2,4,6-trimethylbenzyl)-piperazin-1-yl]-16,17,18,19,28,29-hexahydrorifamycin SV (epimeric mixture) in the form of yellowcoloured crystals that decompose above 250 ; mass spectrum: m/z = 920 (M$^+$ +1) corresponding to the empirical formula $C_{51}H_{73}N_3O_{12}$.

EXAMPLE 17

An approximately 1% solution of NaBH$_4$ in methanol is slowly added dropwise at room temperature, with stirring, to a solution of 3 g of the target product of Example 16 in 50 ml of methanol until the initially deepred colour of the reaction mixture has disappeared completely and the mixture has taken on a pale-yellow colour. The mixture is then diluted with a large amount of water, the reduced material is taken up in ether, the ethereal solution is washed with buffer solution of pH 7 and with a saturated solution of sodium chloride, dried with Na$_2$SO$_4$ and concentrated by evaporation. The almost colourless residue is crystallised several times from ether, resulting in N,15,16,17,18,28,29-octahydro-8-O-pivaloyl-1-deoxy-15-deoxo-1,15-oxy-3-[4-(2,4,6-trimethylbenzyl)-piperazin-1yl]-rifamycin of formula I in which the structural elements —$A_1$-$A_2$—, —$A_3$-$A_4$— and —$A_5$-$A_6$— are each ethylene, X is >N—, alk is methylene, $R_1$ is pivaloyl, $R_2$ is acetyl, $R_3$ and $R_4$ are each hydrogen and $R_5$ is 2,4,6-trimethylphenyl, which is diastereoisomeric to the target product of Example 3. The colourless crystals melt at 234°–235°. $C_{56}H_{81}N_2O_{12}$; mol. wt. 987 (found, MS, DCI). $^1$H-NMR spectrum (360 MHz, DMSO-d6, ppm): no more vinylic H-signals present; differences from the spectrum of the diastereoisomeric compound (target product of Example 3) only in the region of the high field, for example: −0.28 (d, 3H); 0.29 (d, 3H); 0.60 (d, 3H) and 0.78 (d, 3H, 4 Ansa ring methyl groups); 1.40 (d, ~3H, H-30).

EXAMPLE 18

10% solution of freshly prepared 8-O-pivaloyl-3-[4-(2,4,6-trimethylbenzyl)-1-piperazinyl]rifamycin SV in toluene is heated at 170 for 15 minutes in a pressure vessel. The toluene is then evaporated. The material remaining is crystallised from methanol/water. The crystals obtained after crystallising twice, having a melting point of 175°, are 1-deoxy-15-deoxo-1,15-oxy-3-[4(2,4,6-trimethylbenzyl)-1-piperazinyl]-rifamycin of formula I in which the structural elements —$A_1$-$A_2$—, —$A_3$-$A_4$— and —$A_5$-$A_6$— are each vinylene, X is >N—, $R_1$ is hydrogen, $R_2$ is acetyl, $R_3$ and $R_4$ together are a bond, alk is methylene, $R_5$ is 2,4,6-trimethylphenyl and $R_7$ is hydrogen, The starting material can be prepared, for example, as follows:

(a) 1.5 g of pivalic acid chloride (1.13 equivalents) are added dropwise, with stirring, to a solution of 10 g of 3-[4-(2,4,6-trimethylbenzyl)-1-piperazinyl]-rifamycin S in 100 ml of pyridine and the whole is allowed to react for 10 minutes at 20°. 10 ml of methanol are then added to the reaction mixture and the whole is stirred for a further hour and subsequently concentrated to dryness by evaporation in vacuo. The residue is dissolved in ethyl acetate and the ethyl acetate solution is washed with aqueous sodium bicarbonate solution and a saturated solution of sodium chloride, dried over $Na_2SO_4$ and concentrated by evaporation. 8-O-pivaloyl-3-[4-(2,4,6-trimethylbenzyl)-1piperazinyl]-rifamycin S remains, which is crystallised from ether in the form of blue-black crystals having a melting point of 191°–193 (decomposition). (sintering at about 162°, and again at about 175°).

(b) The resulting quinone is dissolved in tetrahydrofuran and while stirring well, there is added to the solution an excess of zinc dust and, dropwise, 1N hydrochloric acid until the reaction mixture has taken on a yellow colour. The reaction mixture is then filtered, the tetrahydrofuran solution is washed twice with saturated sodium chloride solution, dried with sodium sulfate and rapidly concentrated by evaporation in vacuo at low temperature. The yellow residue consists of 8-O-pivaloyl-3-[4-(2,4,6-trimethylbenzyl)-1-piperazinyl]-rifamycin SV, which can be used directly in that form for the ring closure reaction. The material crystallises from ether in the form of orangeyellow crystals that melt at about 165° with decomposition.

EXAMPLE 19

A solution of 1,8-di-O-pivaloyl-3-[2-methyl-4(2,4,6-trimethylbenzyl)-piperazin-1-yl]-rifamycin in 8 ml of 2-methoxyethanol is heated under reflux under nitrogen. After heating for 5 hours, the solvent is removed in vacuo. The crude product is purified by flash chromatography on silica gel, eluted with ethyl acetate/hexane =1:4 to 2:3. 8-O-pivaloyl-1-deoxy-15-deoxo-1,15-oxy-3-[2-methyl-4(2,4,6-trimethylbenzyl)-piperazin-1-yl]Orifamycin of formula I is obtained in which the structural elements —$A_1$-$A_2$—, —$A_3$-$A_4$— and —$A_5$-$A_6$— are each vinylene, $R_1$ is pivaloyl, $R_2$ is acetyl, $R_3$ and $R_4$ together are a bond, alk is methylene, $R_5$ is 2,4,6-trimethylphenyl and $R_7$ is hydrogen, Isomer A (in respect of the $R_7$ (=methyl)-containing C atom of the piperazine ring): melting point: 140° (decomp.), NMR (300 MHz, $CD_3OD$): 6.80 (s, 2H).

Isomer B (in respect of the $R_7$ (=methyl)-containing C atom of the piperazine ring): melting point: 140° (decomp.), NMR (300 MHz, $CD_3OD$): 6.85 (s, 2H).

The starting material can be prepared as follows: At room temperature, a mixture of 1.34 g (5.75 mmol) of 1-trimethyl-3-methyl-piperazine and 1.17 ml (8.17 mmol) of triethylamine in 160 ml of tetrahydrofuran is added dropwise, at a rapid dripping speed, to a solution of 4.45 g (5.75 mmol) of 3-bromo-rifamycin S in 160 ml of tetrahydrofuran. After 10 minutes thin layer chromatography shows that there is no more starting material in the reaction mixture. The solvent is removed under reduced pressure and a dark solid residue is obtained which is chromatographed in a silica gel flash column with methylene chloride and 4% methanol as eluants. In this manner 3-[2-methyl-4-(2,4,6-trimethylbenzyl)-piperazin-1-yl]-rifamycin S is obtained. NMR (270 MHz, $CD_3OD$): 6.78 (2H, s).

A solution of 2.14 g (109.8 mmol) of sodium ascorbate in methanol/water (10 ml each) is added dropwise to a solution of 1 g (1.08 mmol) of 3-[2-methyl-4-(2,4,6-trimethyl-benzyl)-piperazin-yl]-rifamycin S in 40 ml of methanol at room temperature. When the addition is complete, the reaction mixture is stirred for 1 hour, the colour changing from red to orange. Thin-layer chromatography in 10% methanol/methylene chloride shows that there is no more starting material present. Insoluble material is filtered off, and the filtrate is rapidly concentrated to dryness by evaporation. The residue is partitioned between methylene chloride and saturated $NaHCO_3$ solution. The organic extract is washed with a solution of sodium chloride, dried over $MgSO_4$ and concentrated, resulting in the hydroquinone form (SV) as a pair of diastereoisomers in respect of the $R_7$ (=methyl)-containing C atom of the piperazine ring, in the form of a yellow solid. NMR (300 MHz, $CD_3OD$): 6.99 (s, 2H, isomer A); 6.95 (s, 2H, isomer B).

At 0°, 25 mg of dimethylaminopyridine and 0.32 ml of triethylamine are added to a solution of 1.02 g (1.08 mmol) of 3-[2-methyl-4-(2,4,6-trimethylbenzyl)-piperazin-1-yl]-rifamycin SV in 20 ml of methylene chloride and then, dropwise, 0.27 ml (2.20 mmol) of pivaloyl chloride in 6 ml of methylene chloride is added. The reaction mixture is washed with saturated $NaHCO_3$ solution, NaCl solution, dried over MgSO4 and concentrated. The crude product is separated by means of flash chromatography on silica gel, ethyl acetate/hexane 3:1 being used as eluant. There are thus obtained in respect of the $R_7$ (=methyl)-containing C atom of the piperazine ring, 2 isomers of 1,8-di-O-pivaloyl-3-[2-methyl-4-(2,4,6-trimethylbenzyl)-piperazin-1-yl]-rifamycin.

Isomer A: NMR (270 MHz, $CD_3OD$): 6.8 (s, 2H); 1.81 (s, 3H); $R_f$=0.76 ethyl acetate/hexane 1:1)

Isomer B: NMR (270 MHz, CD₃OD): 6.75 (s, 2H); 1.7 (s, 3H); $R_f$=0.71 ethyl acetate/hexane 1:1)

EXAMPLE 20

A solution of 50 mg of isomer A according to Example 19, 10 mg of PtO₂, 0.02 ml of acetic acid and 2 ml of ethyl acetate is hydrogenated for 4 hours at 50 Psi of hydrogen. The catalyst is filtered off and the crude, faintly orange-coloured product is concentrated, and then purified by flash chromatography on silica gel using hexane:ethyl acetate =2:1 to 1:1 as eluant. After trituration with ether 16,17,18,19,28,29-hexahydro-1-11,15-deoxo-1,15-oxy-11-hydroxy-8O-pivaloyl-3-[2-methyl-4-(2,4,6-trimethylbenzyl)-piperazin-1-yl]rifamycin, m.p. 140°-132°, is obtained. NMR (300 MHz, CD₃OD): 5.76 (s, 1H); 2.81 (br. d, 2H) and 2.88 (br. t, 2H).

EXAMPLE 21

In a manner analogous, for example, to that described in Example 1 in the manufacture of the starting material, there is obtained from 1,8-di-O-pivaloyl-3-[4-(4-penten-1-yl)-1-piperazinyl]-rifamycin, 8-O-pivaloyl-1- deoxy-15-deoxo-1,15-oxy-3-[4-(4-penten-1-yl)-1-piperazinyl]-rifamycin of formula I in which the structural elements —A₁-A₂—, —A₃-A₄— and —A₅-A₆— are each vinylene, X is >N—, alk is methylene, R₁ is pivaloyl, R₂ is acetyl, R₃ and R₄ together are a bond, R₅ is 3-butenyl and R₇ is hydrogen. The compound crystallises from methanol in the form of platelets that melt at 140.. C₅₁H₆₉N₂O₁₂; mol. wt.: 915 (found, MS, DCI) ¹H-NMR spectrum (360 MHz, DMSO-d₆): signals of the olefinic side chain in multiplets, centred at: 1.58 (2H), 2.09 (2H), 2.48 (2H) and also 4.95 (together with d of H-25, together with 2H), 5.04 (1H) and 6.86 (1H) ppm.

EXAMPLE 22

The following compounds can be prepared in a manner analogous, for example, to that described in one of the preceding Examples: 8-O-pivaloyl-1-deoxy-15-deoxo-1,15-oxy-3-[4-(2,3-dimethylbenzyl)-piperazin-1-yl)-rifamycin, 8-O-pivaloyl-1-deoxy-15-deoxo-1,15-oxy-3-[4-[1-(2,4,6-trimethylphenyl)-ethyl]-piperazin-1-y1)-rifamycin, 8-O-pivaloyl-1-deoxy-15-deoxo-1,15-oxy-3-[4-[2-(2,4,6-trimethylphenyl)-ethyl]-piperazin-1yl)-rifamycin, 8-O-pivaloyl-1-deoxy-15-deoxo-1,15-oxy-3-[4-[1-(2,4,6-trimethylphenyl)-ethyl]-piperazin-1-yl)-rifamycin, 8-O-pivaloyl-1-deoxy-15-deoxo-1,15-oxy-[4-(2-methoxybenzyl)-piperazin-1-yl)-rifamycin, 8-O-pivaloyl-1-deoxy-15-deoxo-1,15-oxy-[4-(2,4,6-trimethylphenyl)-piperazin-1-yl]-rifamycin.

EXAMPLE 23

Capsules containing as active ingredient 250 mg of, for example, the compound of formula I in which the structural elements —A₁-A₂—, —A₃-A₄— and —A₅-A₆— are each ethylene, X is >N—, alk is methylene, R₁ is pivaloyl, R₂ is acetyl, R₃ and R₄ together are a bond, R₅ is 2,4,6-trimethylphenyl and R₇ is hydrogen, can be prepared as follows:

| Composition (for 1000 capsules): | |
|---|---|
| active ingredient | 250.0 g |
| corn starch | 50.0 g |
| polyvinylpyrrolidone | 15.0 g |
| magnesium stearate | 5.0 g |
| ethanol | q.s. | p The active ingredient and the corn starch are mixed and the mixture is moistened with a solution of the polyvinylpyrrolidone in 50 g of ethanol. The moist mixture is passed through a sieve having a mesh width of 3 mm and dried at 45. The dry granulate is passed through a sieve having a mesh width of 1 mm and mixed with 5 g of magnesium stearate. The mixture is introduced in 0.320 g portions into size 0 dry-fill capsules.

The other compounds prepared according to Examples 1 to 22 can also be used as active components in similar manner.

What is claimed is:

1. A compound of formula

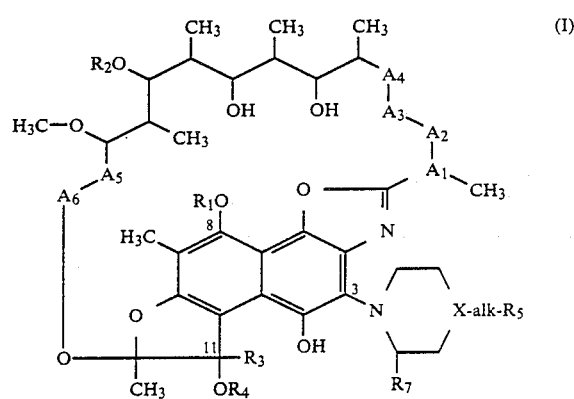

or a pharmaceutically acceptable salt thereof in which the structural elements —A₁-A₂—, —A₃-A₄— and —A₅-A₆— are each ethylene or vinylene or the elements —A₁-A₂—, and —A₃-A₄— are each ethylene and —A₅-A₆— is vinylene, X is >CR₆— or >N— and R₆ is alkyl or hydrogen, alk is C₁-C₁₂alkylene, C₃-C₇alkenylene or C₃-C₇alkynylene, the multiple bond being located in a position higher than the α-position to the piperazine nitrogen (X—>N—), R₁ is unsubstituted or halo- or phenyl-substituted branched or straight chain C₂-C₈alkanoyl benzoyl, naphthoyl or monocyclic 5-or 6-membered monoaza, monooxa, or monothiaaroyl, C₁-C₇alkoxycarbonyl, or aminocarbonyl that is unsubstituted or mono- or disubstituted by C₁-C₇alkyl, R₂ is hydrogen or acetyl, R₃ and R₄ togerher are a bond or each is hydrogen, R₅ is hydrogen, C₃-C₇cycloalkyl, C₃-C₇cycloalkenyl, C₃-C₇cycloalkynyl, phenyl, biphenylyl, naphthyl, monocyclic 5- or 6-membered monoaza-, monooxa, or monothia-aryl and R₇ is hydrogen or C₁-C₇alkyl, each of the aromatic radicals, independently of the others, being unsubstituted or mono- or poly-bustituted by halogen, C₁-C₇alkyl, C₁-C₇alkoxy, hydroxy, C₂-C₈alkanoyloxy, trifluoromethyl and-/or nitro, with the proviso that when —A₁-A₂—, —A₃-A₄— and —A₅-A₆— are each vinylene, X is >N—, R₁ is hydrogen or trialkylacetyl, R₂ is hydrogen or acetyl, R₃ and R₄ together are a bond and alk is methylene and R₅ is other than 2,6-dimethyl-4-alkylphenyl.

2. A compound according to claim 1 of formula I, or a pharmaceutically salt thereof, in which —A₁-A₂—, —A₃-A₄—, —A₅-A₆—, R₂, R₃ and R₄ have the measnings given, X is >C(R₆) or >N— and R₆ is hydrogen or C₁-C₇alkyl, alk is C₁-C₁₂alkylene, C₃-C₇alkenylene or C₃-C₇alkynylene, the multiple bond being located in a position higher than the α-position to the piperazine nitrogen atom, R₁ is unsubstituted or halo- or phenyl-substituted $C_2$–$C_8$alkanoyl, benzoyl, naphthoyl or monocyclic 5- or 6-membered monoaza-, monooxa- or monothia-aroyl, $C_1$–$C_7$alkoxycarbonyl, or aminocarbonyl that is unsubstituted or mono- or di-substituted by $C_1$–$C_7$alkyl, $R_5$ is hydrogen, $C_3$–$C_7$cycloalkyl, $C_3$–$C_7$cycloalkenyl, $C_3$–$C_7$cycloalkynyl, phenyl, biphenylyl, naphthyl, pyrrolyl, N-$C_1$–$c_7$alkylpyrrolyl, pyridyl, 1-oxidopyridyl, furyl or theinyl, and $R_7$ is hydrogen or $C_1$–$C_7$alkyl, each of the aromatic radicals, independently of the others, being unsubstituted or mono-or poly-substituted by halogen, $C_1$–$C_7$alkyl, $C_1$–$C_7$alkoxy, hydroxy, $C_2$–$C_8$-alkanoyloxy, trifluoromethyl and/or nitro.

3. A compound according to claim 1 of formula I, or a pharmaceutically salt thereof, in which —$A_1$-$A_2$—, —$A_3$-$A_4$—, —$A_5$-$A_6$—, $R_2$, $R_3$ and $R_4$ have the meanings given, X is >CH— or >N—, alk is $C_1$–$C_7$alkylene, $R_1$ is $C_2$–$C_8$alkanoyl that is unsubstituted or substituted by halogen or by phenyl which may contain halogen, $C_1$–$C_7$alkyl, $C_1$–$C_7$alkoxy, hydroxy, $C_2$–$C_8$alkanoyloxy, trifluoromethyl and/or nitro, unsubstituted or halo-, $C_1$–$C_7$alkyl-, $C_1$–$C_7$alkoxy-, hydroxy-, $C_2$–$C_8$alkanoyloxyoxy, trifluoromethyl- and/or nitro-substituted benzoyl, naphthoyl or monocyclic 5- or 6-membered monoaza-, monooxa- or monothia-aroyl, $C_1$–$C_7$alkoxycarbonyl, or aminocarbonyl that is unsubstituted or mono- or di-substituted by $C_1$–$C_7$alkyl, $R_5$ is hydrogen, $C_3$–$C_7$cycloalkyl, or phenyl, biphenylyl or naphthyl each of which is unsubstituted or mono- or poly-substituted by halogen, $C_1$–$C_7$alkyl, $C_1$–$C_7$alkoxy, hydroxy, $C_2$–$C_8$alkanoyloxy, trifluoromethyl and/or by nitro, and $R_7$ is hydrogen.

4. A compound according to claim 1 of formula I, and or a pharmaceutically salt thereof, in which —$A_1$-$A_2$—, —$A_3$-$A_4$—, —$A_5$-$A_6$—, $R_2$, $R_3$ and $R_4$ have the meanings given, X is >C($R_6$) or >N— and $R_6$ is hydrogen or $C_1$–$C_7$alkyl, alk is $C_1$–$C_{12}$alkylene, such as $C_1$–$C_7$alkylene, $C_3$–$C_7$alkenylene or $C_3$–$C_7$alkynylene, the multiple bond being located in a position higher than the α-position to the piperazine nitrogen atom, $R_1$ is hydrogen or $C_3$–$C_6$alkanoyl, $R_5$ is hydrogen, $C_3$–$C_7$cycloalkyl, $C_3$–$C_7$cycloalkenyl, or phenyl, biphenylyl, naphthyl, thienyl, furyl or pyridyl each of which unsubstituted or substituted by halogen, $C_1$–$C_7$alkyl, $C_1$–$C_7$alkoxy and/or by trifluoromethyl, and $R_7$ is hydrogen or $C_1$–$C_7$alkyl.

5. A compound according to claim 1 of formula I, and salts thereof, in which —$A_1$-$A_2$—, —$A_3$-$A_4$— and —$A_5$-$A_6$— are each ethylene, X is >N—, $R_1$ is pivaloyl, $R_2$ is acetyl, $R_3$ and $R_4$ together are a bond or each is hydrogen, alk-$R_5$ is 2,4,6-trimethylbenzyl, and $R_7$ is hydrogen.

6. 16,17,18,19-tetrahydro-8-O-pivaloyl-1deoxy-15deoxo-1,15-oxy-3-[4-(2,4,6-trimethylbenzyl)-piperazin-1-yl]-rifamycin or a salt thereof according to claim 1.

7. 16,17,18,19,28,29-tetrahydro-8-O-pivaloyl-1deoxy-15deoxo-1,15-oxy-3-[4-(2,4,6-trimethylbenzyl)-piperazin-1-yl]-rifamycin or a salt thereof according to claim 1.

8. 8-O-pivaloyl-1deoxy-15deoxo-1,15-oxy-3-[4-napthyl-methyl)-piperazin-1-yl]-rifamycin or a salt thereof according to claim 1.

9. 8-O-pivaloyl-1-deoxy-15-deoxo-1,15-oxy-3-(4-isobutylpiperazin-1-yl)-rifamycin or a salt thereof according to claim 1.

10. N,15,16,17,18,19,28,29-octahydro-8-O-pivaloyl-1-deoxy-15-deoxo-1,15-oxy-3-(4-isobutyl-1-piperazinyl)-rifamycin or a salt thereof according to claim 1.

11. 8-O-pivaloyl-1-deoxy-15-deoxo-1,15-oxy-3-[4-(phenylbenzyl)-1-piperazinyl]-rifamycin or a salt according to claim 1.

12. N,15-dihydro-8-O-pivaloyl-1-deoxy-15-deoxo-1,15-oxy-3-[4-(2,4,6-trimethylbenzyl)-1-piperazinyl]-rifamycin or a salt thereof according to claim 1.

13. 8-O-pivaloyl-1-deoxy-15-deoxo-1,15-oxy-3-[4-(2,5-dimethylbenzyl)-1-piperazinyl]-rifamycin or a salt thereof according to claim 1.

14. 8-O-pivaloyl-1-deoxy-15-deoxo-1,15-oxy-3-(4-benzyl-1-piperazinyl)-rifamycin or a salt thereof according to claim 1.

15. 8-O-pivaloyl-1-deoxy-15-deoxo-1,15-oxy-3-(4-cyclohexylmethyl-1-piperazinyl)-rifamycin or a salt thereof according to claim 1.

16. 8-O-pivaloyl-1-deoxy-15-deoxo-1,15-oxy-3-[4-(cyclohex-3-en-1-ylmethyl)-1-piperazinyl)-rifamycin or a slat thereof according to claim 1.

17. 8-O-pivaloyl-1-deoxy-15-deoxo-1,15-oxy-3-[2-methyl-4-(2,4,6-trimethylbenzyl)-piperazin-1-yl)-rifamycin or a salt thereof according to claim 1.

18. A compound according to claim 1, in the form of a pharmaceutically acceptable salt.

19. A compound according to claim 1 in the form of an ascorbic acid salt.

20. A compound according to claim 1 in the form of the (16S) isomer.

21. A compound according to claim 1 in the form of the (16R) isomer.

22. A method of treating hyperlipidaemia and arteriosclerosis which comprises administering a compound according to claim 1, or a pharmaceutically acceptable salt thereof in a therapeutically effective amount.

23. A compound according to claim 1 of formula I or a pharmaceutically acceptable salt thereof, in which —$A_1$-$A_2$—, —$A_3$-$A_4$— and —$A_5$-$A_6$—, $R_3$ and $R_4$ have the meanings given, X is >CH— or N—, $R_1$ is $C_3$–$C_6$alkanoyl, $R_2$ is acetyl, alk is $C_3$–$C_7$alkylene, and $R_5$ or cycloalkyl, $C_3$–$C_6$cycloalkenyl, unsubstituted or $C_1$–$C_4$alkyl-substituted, phenyl, biphenylyl, napthyl, or thienyl, and $R_7$ is hydrogen or $C_1$–$C_4$alkyl.

24. A compound according to claim 1 of formula I, or a pharmaceutically acceptable salt thereof, in which —$A_1$-$A_2$—, —$A_3$-$A_4$—, —$A_5$-$A_6$—, $R_3$ and $R_4$ have the meanings given, $R_1$ is hydrogen or $C_2$–$C_8$alkanoyl, $R_2$ is acetyl, X is >N—, alk is $C_1$–$C_7$alkylene, $R_5$ is hydrogen, $C_3$–$C_7$cycloalkyl, or phenyl, biphenyly or naphthyl each of which is unsubstituted or mono- or poly-substituted by $C_1$–$C_4$alkyl or halogen, and $R_7$ is hydrogen.

25. A compound according to claim 1 of formula I or a pharmaceutically acceptable salt thereof, in which the structural elements —$A_1$-$A_2$—, —$A_3$-$A_4$— and —$A_5$-$A_6$— have the same meanings given, $R_1$ is branched $C_3$–$C_6$-alkanoyl, $R_2$ is acetyl, $R_3$ and $R_4$ have the meanings given, X is >N—, alk is $C_1$–$C_4$alkylene, $R_5$ is $C_3$–$C_7$cycloalkyl, $C_3$–$C_7$cycloalkenyl, or phenyl mono- or poly-substituted by $C_1$–$C_4$alkyl and $R_7$ is hydrogen or $C_1$–$C_4$alkyl.

26. A compound according to claim 1 of formula I or a pharmaceutically acceptable salt thereof, in which the structural elements —$A_1$-$A_2$—, —$A_3$-$A_4$— and —$A_5$-$A_6$— and the variables $R_3$ and $R_4$ have the meanings given, alk is $C_1$-$C_4$alkylene, $R_1$ is hydrogen or branched $C_3$-$C_6$-alkanoyl, $R_2$ is acetyl, X is >N—, $R_5$ is hydrogen, $C_3$-$C_6$cycloalkyl, phenyl or 2,4,6-tri-$C_1$-$C_4$-alkylphenyl and $R_7$ is hydrogen.

27. A compound according to claim 1 of formula I or a pharmaceutically acceptable salt thereof, in which the structural elements —$A_1$-$A_2$—, —$A_3$-$A_4$— and —$A_5$-$A_6$— have the meanings given, X is >N—, $R_2$ is hydrogen or acetyl, $R_3$ and $R_4$ together are a bond, and alk is $C_1$-$C_4$alkylene, and $R_5$ is hydrogen or alk is methylene and $R_5$ is 2,4,6-tri-$C_1$-$C_4$alkylphenyl, and $R_7$ is hydrogen.

28. A compound according to claim 1 of formula I or a pharmaceutically acceptable salt thereof, in which the structural elements —$A_1$-$A_2$—, —$A_3$-$A_4$— and —$A_5$-$A_6$— have the meanings given, X is >N—, $R_2$ is acetyl, $R_3$ and $R_4$ together are a bond or each is hydrogen, and alk is $C_1$-$C_4$alkylene, and $R_5$ is hydrogen or alk is methylene and $R_5$ is 2,4,6-tri-$C_1$-$C_4$alkylphenyl, and $R_7$ is $C_1$-$C_7$alkyl.

29. A compound according to claim 1 of formula I or a pharmaceutically acceptable salt thereof, in which the structural elements —$A_1$-$A_2$—, —$A_3$-$A_4$— and —$A_5$-$A_6$— are each vinylene, or the elements —$A_1$-$A_2$—, —$A_3$-$A_4$— are buta-1,3-dien-1,4-diyl and —$A_5$-$A_6$— is ethylene, X is >CH—, alk is $C_1$-$C_4$alkylene, $R_1$ is branched $C_3$-$C_6$alkanoyl, $R_2$ is acetyl, $R_3$ and $R_4$ together are a bond and $R_5$ is hydrogen, cyclohexyl or phenyl, and $R_7$ is hydrogen.

30. A compound according to claim 1 of formula I or a pharmaceutically acceptable salt thereof, in which the structural elements —$A_1$-$A_2$—, —$A_3$-$A_4$— and —$A_5$-$A_6$— are each vinylene, or the elements —$A_1$-$A_2$-$A_3$-$A_4$— are buta-1,3-dien01,4-diyl and —$A_5$-$A_6$— is ethylene, X is >N—, $R_1$ is hydrogen or branched $C_3$-$C_6$alkanoyl, $R_2$ is acetyl, $R_3$ and r4 together are a bond, alk is $C_1$-$C_4$alkylene, and $R_5$ is 2,4,6-tri-$C_1$-$C_4$alkylphenyl and $R_7$ is hydrogen.

31. A compound according to claim 1 of formula I or a pharmaceutically acceptable salt thereof, in which X is >N—, —$A_1$-$A_2$— and —$A_3$-$A_4$— are each ethylene and —$A_5$-$A_6$— is vinylene or ethylene, $R_1$ is branched $C_3$-$C_6$alkanoyl $R_2$ is acetyl, $R_3$ and $R_4$ together are a bond or each is hydrogen, alk is $C_1$-$C_4$alkylene and $R_5$ is 2,4,6-trimethylphenyl, or alk is $C_1$-$C_4$alkylene and $R_5$ is hydrogen, and $R_7$ is hydrogen.

32. A compound according to claim 1 of formula I or a pharmaceutically acceptable salt thereof, in which —$A_1$-$A_2$—, —$A_3$-$A_4$—, —$A_5$-$A_6$—, $R_3$ and $R_4$ have the meanings given, X is >CH— or N—, $R_1$ is pivaloyl, $R_2$ is acetyl, alk is 2-methyl-1,3-propylene and $R_5$ is hydrogen, or alk is methylene and $R_5$ is cyclohexyl, cyclohex-3-en-1yl, 2,5-dimethyl- or 2,4,6-trimethylphenyl, 4-biphenylyl, 1-naphthyl, or 2-thienyl, and $R_7$ is hydrogen or methyl.

33. A compound according to claim 1 of formula I, or a pharmaceutically acceptable salt thereof, in which —$A_1$-$A_2$—, —$A_3$-$A_4$—, —$A_5$-$A_6$—, $R_3$ $R_4$ have the meanings given, $R_1$ is hydrogen or branched $C_3$-$C_6$alkanoyl, $R_2$ is acetyl, X is >N—, alk is $C_1$-$C_4$alkylene, $R_5$ is hydrogen, $C_3$-$C_7$cycloalkyl, or phenyl, biphenylyl or naphthyl each of which is unsubstituted or mono- or poly-substituted by $C_1$-$C_4$alkyl or halogen, and $R_7$ is hydrogen.

34. A compound according to claim 1 of formula I or a pharmaceutically acceptable salt thereof, in which the structural elements —$A_1$-$A_2$—, —$A_3$-$A_4$— and —$A_5$-$A_6$— have the meanings given, $R_1$ is pivaloyl, $R_2$ is acetyl, $R_3$ and $R_4$ have the meanings given, X is >N—, alk is methylene, $R_5$ is cyclohexyl, cyclohex-3-en-1-yl, or 2-methylphenyl, 2,3-, 2,5-, or 2,6-dimethylphenyl or 2,4,6-trimethylphenyl, and $R_7$ is hydrogen or methyl.

35. A compound according to claim 1 of formula I or a pharmaceutically acceptable salt thereof, in which the structural elements —$A_1$-$A_2$—, —$A_3$-$A_4$— and —$A_5$-$A_6$— and the variables $R_3$ and $R_4$ have the meanings given, alk is methylene, 2,3-propylene or 2-methyl-1,3-propylene, $R_1$ is hydrogen or pivaloyl, $R_2$ is acetyl, X is >N—, $R_5$ is hydrogen, cyclohexyl, phenyl or 2,4,6-trimethylphenyl, and $R_7$ is hydrogen.

36. A compound according to claim 1 of formula I or a pharmaceutically acceptable salt thereof, in which the structural elements —$A_1$-$A_2$—, —$A_3$-$A_4$— and —$A_5$-$A_6$— have the meanings given, X is >N—, Rhd 2 is hydrogen or acetyl, $R_3$ and $R_4$ together are a bond, and alk is 2-methyl-1,3-propylene and $R_5$ is hydrogen, or alk is methylene and $R_5$ is 2,4,6-trimethylphenyl, and $R_7$ is in each case hydrogen.

37. A compound according to claim 1 of formula I, or a pharmaceutically acceptable salt thereof, in which the structural elements —$A_1$-$A_2$—, —$A_3$-$A_4$— and —$A_5$-$A_6$— have the meanings given, X is >N—, $R_2$ is acetyl, $R_3$ and $R_4$ together are a bond or each is hydrogen, and alk is 2-methyl-1,3-propylene, and $R_5$ is hydrogen, or alk is methylene and $R_5$ is 2,4,6-trimethylphenyl, and $R_7$ is methyl.

38. A compound according to claim 1 of formula I or a pharmaceutically acceptable salt in which the structural elements —$A_1$-$A_2$—, —$A_3$-$A_4$— and —$A_5$-$A_6$— are each vinylene, or the elements —$A_1$-$A_2$-$A_3$-$A_4$— are buta-1,3-dien-1,4-diyl and —$A_5$-$A_6$— is ethylene, X is >CH—, alk is methylene or 2,3-propylene, $R_1$ is pivaloyl, $R_2$ is acetyl, $R_3$ and $R_4$ together are a bond and $R_5$ is hydrogen, cyclohexyl or phenyl, and $R_7$ is hydrogen.

39. A compound according to claim 1 of formula I, or a pharmaceutically acceptable salt in which the structural elements —$A_1$-$A_2$—, —$A_3$-$A_4$— and —$A_5$-$A_6$— are each vinylene, or the elements —$A_1$-$A_2$-$A_3$-$A_4$— are buta-1,3-dien-1,4-diyl and —$A_5$-$A_6$— is ethylene, X is >N—, $R_1$ is hydrogen or pivaloyl, $R_2$ is acetyl, $R_3$ and $R_4$ together are a bond, alk is 2-methyl-1,3-propyl, and $R_5$ is hydrogen, or alk is methylene and $R_5$ is 2,4,6-trimethylphenyl, and $R_7$ is hydrogen.

40. A compound according to claim 1 of formula I or a pharmaceutically acceptable salt in which X is >N—, —$A_1$-$A_2$—, —$A_3$-$A_4$— are each ethylene and —$A_5$-$A_6$— is vinylene or ethylene, $R_1$ is pivaloyl, $R_2$ is acetyl, $R_3$ and $R_4$ together are a bond or each is hydrogen, alk is methylene, and $R_5$ is 2,4,6-trimethylphenyl or alk is 2-methyl-1,3-propylene, and $R_5$ is hydrogen, and $R_7$ is hydrogne.

41. 16,17,18,19,28,29-hexahydro-8-O-pivaloyl-1-deoxy-11,15-deoxo-1,15-oxy-11-hydroxy-3-[4-(2,4,6-trimethylbenzyl)-piperazin-1yl]-rifamycin or a pharmaceutically acceptable salt thereof according to claim 1.

42. 16,17,18,19-tetrahydro-8-O-pivaloyl-1-deoxy-11,15-deoxo-1,15-oxy-11-hydroxy-3-[4-(2,4,6-trimethylbenzyl)-1-piperazinyl]-rifamycin or a pharmaceutically acceptable salt thereof according to claim 1.

43. 16,17,18,19,28,29-hexahydro-1-deoxy-11,15-deoxo-1,15-oxy-11-hydroxy-8-O-pivaloyl-3-[2-methyl-4-(2,4,6-trimethylbenzyl)-1-piperazin-1yl)-rifamycin or a pharmaceutically acceptable salt thereof according to claim 1.

44. A pharmaceutical preparation comprising a hypolipidaemically effective amount of a compound according to claim 1 or a pharmaceutically acceptable salt thereof together with customary adjuncts and additives.

* * * * *

UNITED STATES PATENT AND TRADEMARK OFFICE
CERTIFICATE OF CORRECTION

PATENT NO. : 5,003,070  
DATED : March 26, 1991  
INVENTOR(S) : Kump et al.

It is certified that error appears in the above-identified patent and that said Letters Patent is hereby corrected as shown below:

In the specification:

Col. 28, line 6 should read:

-- [2-methyl-4(2,4,6-trimethylbenzyl)-piperazin-1-yl]-rifa--

Col. 28, line 11 should read:

-- thylphenyl and $R_7$ is methyl.--

In the claims:
COLUMN 30

Claim 1, line 39 should read:

-- the piperazine nitrogen (X=>N-), $R_1$ is unsubstituted --

Claim 1, line 42 should read:

-- ic 5-or 6-membered monoaza-, or monothia-

Claim 1, line 45, should read:

-- $R_2$ is hydrogen or acetyl, $R_3$ and $R_4$ together are a bond --

Claim 1, line 49, should read:

-- monoaza-, monooza-, or monothia-aryl and $R_7$ is hydro- --

UNITED STATES PATENT AND TRADEMARK OFFICE
CERTIFICATE OF CORRECTION

PATENT NO. : 5,003,070

DATED : March 26, 1991

INVENTOR(S) : Kump et al.

It is certified that error appears in the above-identified patent and that said Letters Patent is hereby corrected as shown below:

In the claims:

COLUMN 30

Claim 1, line 52 should read:

--or poly-substituted by halogen, $C_1$-$C_7$ alkyl, $C_1$-$C_7$ alk- --

Claim 1, line 58 should read:

-- methylene, $R_5$ is other than 2,6-dimethyl-4-alkylphe- --

Claim 2, line 62 should read:

-- -$A_3$-$A_4$-, -$A_5$-$A_6$-, $R_2$, $R_3$ and $R_4$ have the mean- --

Claim 2, col. 31, line 8 should read:

-- oxidopyridyl, furyl or thienyl, and $R_7$ is hydrogen or --

COLUMN 31

Claim 3, line 23, should read:

--anoyloxy-, trifluoromethyl- and/or nitro-substituted --

Claim 4, line 37 should read:

--or $C_1$-$C_7$ alkyl, alk is $C_1$-$C_{12}$ alkylene, --

UNITED STATES PATENT AND TRADEMARK OFFICE
CERTIFICATE OF CORRECTION

PATENT NO. : 5,003,070

DATED : March 26, 1991

INVENTOR(S) : Kump et al.

It is certified that error appears in the above-identified patent and that said Letters Patent is hereby corrected as shown below:

COLUMN 31

Claim 4, line 38 should read:
  --$C_3$-$C_7$ alkenylene or $C_3$-$C_7$ alkynylene, the --

Claim 7, line 58 should read:
  --16, 17, 18, 19, 28, 29-hexahydro-8-O-pivaloyl-1-deoxy- --

Claim 10 should read:
  -- 16, 17, 18, 19, 28, 29-Hexahydro-8-O-pivaloyl-1-deoxy-1,
     15-oxy-11-hydroxy-3-(4-isobutyl-1-piperazinyl)-rifamycin
     or a salt thereof according to claim 1. --

COLUMN 32,
Claim 12 should read:

-- 8-O-Pivaloyl-1-deoxy-11, 15-deoxo-1, 15-oxy-11-hydroxy-3-
     [4-(2,4,6-trime-thylbenzyl)-1-piperazinyl]-rifamycin or
     a salt thereof according to claim 1. --

Claim 23, line 40, "-$A_1$-$A_2$-, -$A_3$-$A_4$- and -$A_5$-$A_6$-, $R_3$ and $R_4$" should read -- -$A_1$-$A_2$-, $A_3$-$A_4$-, -$A_5$-$A_6$-, $R_3$ and $R_4$ --.

Claim 23, line 43 should read:
  -- $R_5$ is hydrogen or alk is $C_1$-$C_4$ alkylene, and $R_5$ is $C_3$-$C_6$--

UNITED STATES PATENT AND TRADEMARK OFFICE
CERTIFICATE OF CORRECTION

PATENT NO. : 5,003,070

DATED : March 26, 1991

INVENTOR(S) : Kump et al.

It is certified that error appears in the above-identified patent and that said Letters Patent is hereby corrected as shown below:

In the claims:

COLUMN 32

Claim 24, line 52 should read:

--hydrogen, $C_3$-$C_7$ cycloalkyl, or phenyl, biphenylyl or --

COLUMN 33

Claim 30, line 34 should read:

--   --$A_1$-$A_2$-$A_3$-$A_4$- are buta-1,3-dien-1,4-diyl and  --

Claim 30, line 36 should read:

-- branched $C_3$-$C_6$ alkanoyl, $R_2$ is acetyl, $R_3$ and $R_4$ to- --

Claim 33, line 56 should read:

--   --$A_1$-$A_2$-,-$A_3$-$A_4$-,-$A_5$-$A_6$-, $R_3$, $R_4$ have the  --

UNITED STATES PATENT AND TRADEMARK OFFICE
CERTIFICATE OF CORRECTION

PATENT NO. : 5,003,070

DATED : March 26, 1991

INVENTOR(S) : Kump et al.

It is certified that error appears in the above-identified patent and that said Letters Patent is hereby corrected as shown below:

COLUMN 32

Claim 40, line 52 should read:

-- $R_7$ is hydrogen.--

Signed and Sealed this

Second Day of February, 1993

Attest:

STEPHEN G. KUNIN

*Attesting Officer*  Acting Commissioner of Patents and Trademarks